United States Patent
Chong et al.

(10) Patent No.: US 11,632,981 B2
(45) Date of Patent: Apr. 25, 2023

(54) HEAT-NOT-BURN DEVICE AND METHOD

(71) Applicant: CQENS Technologies Inc., Minneapolis, MN (US)

(72) Inventors: Alexander Chinhak Chong, St. Louis Park, MN (US); William Bartkowski, Edina, MN (US); David Crosby, Watsonville, CA (US); David Wayne, Aptos, CA (US)

(73) Assignee: CQENS TECHNOLOGIES, INC., Minneapolis, MN (US)

( * ) Notice: Subject to any disclaimer, the term of this patent is extended or adjusted under 35 U.S.C. 154(b) by 0 days.

(21) Appl. No.: 17/001,348

(22) Filed: Aug. 24, 2020

(65) Prior Publication Data

US 2020/0383377 A1  Dec. 10, 2020

Related U.S. Application Data

(63) Continuation of application No. 16/022,482, filed on Jun. 28, 2018, now Pat. No. 10,750,787.
(Continued)

(51) Int. Cl.
*A24F 47/00* (2020.01)
*A24D 1/00* (2020.01)
(Continued)

(52) U.S. Cl.
CPC ............... *A24D 1/002* (2013.01); *A24C 5/01* (2020.01); *A24D 1/02* (2013.01); *A24D 1/20* (2020.01);
(Continued)

(58) Field of Classification Search
CPC ............................... A24D 1/20; A24F 40/465
See application file for complete search history.

(56) References Cited

U.S. PATENT DOCUMENTS

| 2,991,788 | A | 7/1961 | Alvin |
| 3,292,634 | A | 12/1966 | Beucler |

(Continued)

FOREIGN PATENT DOCUMENTS

| AU | 2015261876 A1 | 7/2016 |
| AU | 2015261877 A1 | 7/2016 |

(Continued)

OTHER PUBLICATIONS

Patent Cooperation Treaty, "Notification of Transmittal of the International Search Report and the Written Opinion of the International Searching Authority or the Declaration," PCT/US19/122204, dated May 14, 2019, 34 pages.

(Continued)

*Primary Examiner* — Eric Yaary
(74) *Attorney, Agent, or Firm* — Cislo & Thomas, LLP

(57) ABSTRACT

A device and method for converting a consumable into an aerosol with high heat without burning the consumable by packaging the consumable containing an internal susceptor inside an encasement with an induction heating element wrapped around the consumable-containing package to heat the susceptor using a magnetic field generated by the induction heating element. Combustion of the consumable-containing package is minimized by limiting air inside the consumable-containing package by coating a plurality of holes in the encasement material that melts at high temperatures. The coating may also include a flavoring.

23 Claims, 20 Drawing Sheets

Related U.S. Application Data

(60) Provisional application No. 62/613,355, filed on Jan. 3, 2018.

(51) Int. Cl.

| | | |
|---|---|---|
| *A24F 7/04* | (2006.01) | |
| *A24D 3/10* | (2006.01) | |
| *A24D 1/02* | (2006.01) | |
| *A61M 15/06* | (2006.01) | |
| *A61M 15/00* | (2006.01) | |
| *H05B 6/10* | (2006.01) | |
| *A24C 5/01* | (2020.01) | |
| *A24D 1/20* | (2020.01) | |
| *A24D 3/17* | (2020.01) | |
| *A24F 40/465* | (2020.01) | |
| *H04W 4/80* | (2018.01) | |
| *A24F 40/20* | (2020.01) | |
| *H04M 1/72412* | (2021.01) | |
| *A24F 40/53* | (2020.01) | |

(52) U.S. Cl.
CPC ............... *A24D 3/10* (2013.01); *A24D 3/17* (2020.01); *A24F 7/04* (2013.01); *A24F 40/465* (2020.01); *A61M 15/0021* (2014.02); *A61M 15/06* (2013.01); *H05B 6/105* (2013.01); *A24F 40/20* (2020.01); *A24F 40/53* (2020.01); *A61M 2205/3584* (2013.01); *A61M 2205/3653* (2013.01); *H04M 1/72412* (2021.01); *H04W 4/80* (2018.02)

(56) References Cited

U.S. PATENT DOCUMENTS

| | | |
|---|---|---|
| 3,765,428 A | 10/1973 | Beam |
| 3,834,399 A | 9/1974 | Beam |
| 5,129,409 A | 7/1992 | White et al. |
| 5,613,505 A | 4/1997 | Campbell |
| 9,399,110 B2 | 7/2016 | Goodman et al. |
| 9,675,109 B2 | 6/2017 | Monsees et al. |
| 9,717,277 B2 | 8/2017 | Mironov |
| 9,888,719 B2 | 2/2018 | Cadieux et al. |
| 9,894,936 B2 | 2/2018 | Krietzman |
| 9,913,950 B2 | 3/2018 | Goodman et al. |
| 10,051,890 B2 | 8/2018 | Mironov et al. |
| 10,104,912 B2 | 10/2018 | Sur |
| 10,362,804 B2 | 7/2019 | Bessant et al. |
| 10,362,806 B2 | 7/2019 | Cadieux et al. |
| 10,499,690 B2 | 12/2019 | Thorens |
| 10,524,508 B2 | 1/2020 | Sur et al. |
| 10,588,347 B2 | 3/2020 | Malgat et al. |
| 10,660,368 B2 | 5/2020 | Thorens |
| 10,820,630 B2 | 11/2020 | Davis et al. |
| 10,863,770 B2 | 12/2020 | Mironov et al. |
| 10,869,504 B2 | 12/2020 | Mironov et al. |
| 10,918,135 B2 | 2/2021 | Thorens |
| 10,945,456 B2 | 3/2021 | Mironov et al. |
| 10,945,466 B2 | 3/2021 | Mironov et al. |
| 10,952,469 B2 | 3/2021 | Mironov |
| 10,952,472 B2 | 3/2021 | Thorens |
| 10,966,462 B2 | 4/2021 | Alarcon et al. |
| 10,986,869 B2 | 4/2021 | Zinovik et al. |
| 11,019,848 B2 | 6/2021 | Rojo-Caideron |
| 11,033,055 B2 | 6/2021 | Fraser et al. |
| 11,058,141 B2 | 7/2021 | Sanna et al. |
| 11,083,213 B2 | 8/2021 | Malgat et al. |
| 11,116,916 B2 | 9/2021 | Thorens |
| 11,116,920 B2 | 9/2021 | Thorens |
| 11,140,923 B2 | 10/2021 | Courbat et al. |
| 11,141,548 B2 | 10/2021 | Ballesteros Gomez et al. |
| 11,160,309 B2 | 11/2021 | Mironov et al. |
| 2004/0025865 A1 | 2/2004 | Nichols et al. |
| 2008/0156319 A1 | 7/2008 | Avni |
| 2010/0059070 A1 | 3/2010 | Potter et al. |
| 2011/0162187 A1 | 7/2011 | Patel |
| 2011/0277780 A1 | 11/2011 | Terry |
| 2012/0298123 A1 | 11/2012 | Woodcock et al. |
| 2012/0325226 A1 | 12/2012 | Snaidr et al. |
| 2014/0360515 A1 | 12/2014 | Vasiliev et al. |
| 2015/0040925 A1 | 2/2015 | Saleem et al. |
| 2015/0245669 A1* | 9/2015 | Cadieux ............... A24F 40/50 131/329 |
| 2015/0320116 A1 | 11/2015 | Bleloch et al. |
| 2016/0044963 A1 | 2/2016 | Saleem |
| 2016/0135495 A1* | 5/2016 | Poget ................. A24D 1/002 131/336 |
| 2016/0150825 A1 | 6/2016 | Mironov et al. |
| 2016/0211693 A1 | 7/2016 | Stevens et al. |
| 2016/0295921 A1* | 10/2016 | Mironov ............... A24D 1/20 |
| 2016/0295922 A1 | 10/2016 | John et al. |
| 2016/0324216 A1 | 11/2016 | Li et al. |
| 2016/0325055 A1 | 11/2016 | Cameron |
| 2017/0027233 A1 | 2/2017 | Mironov |
| 2017/0055584 A1 | 3/2017 | Blandino et al. |
| 2017/0055585 A1 | 3/2017 | Fursa et al. |
| 2017/0055587 A1 | 3/2017 | Zinovik et al. |
| 2017/0079326 A1 | 3/2017 | Mironov |
| 2017/0079330 A1 | 3/2017 | Mironov et al. |
| 2017/0119048 A1 | 5/2017 | Kaufman et al. |
| 2017/0156403 A1 | 6/2017 | Gill et al. |
| 2017/0245550 A1 | 8/2017 | Freelander |
| 2017/0251722 A1 | 9/2017 | Kobal et al. |
| 2017/0251723 A1 | 9/2017 | Kobal et al. |
| 2017/0280779 A1 | 10/2017 | Qiu |
| 2017/0311648 A1 | 11/2017 | Gill et al. |
| 2017/0340010 A1 | 11/2017 | Bilat et al. |
| 2018/0007974 A1 | 1/2018 | Thorens |
| 2018/0020733 A1 | 1/2018 | Jochnowitz |
| 2018/0029782 A1 | 2/2018 | Zuber et al. |
| 2018/0192700 A1 | 7/2018 | Fraser et al. |
| 2018/0263286 A1 | 9/2018 | Reevell |
| 2019/0045837 A1 | 2/2019 | Spencer |
| 2019/0075845 A1 | 3/2019 | Malgat et al. |
| 2019/0098927 A1 | 4/2019 | Mironov |
| 2019/0182909 A1 | 6/2019 | Fursa et al. |
| 2019/0200677 A1 | 7/2019 | Chong et al. |
| 2019/0269174 A1 | 9/2019 | Robert et al. |
| 2019/0281892 A1 | 9/2019 | Hejazi et al. |
| 2019/0364973 A1* | 12/2019 | Kaufman ............... H05B 6/105 |
| 2019/0380391 A1 | 12/2019 | Reevell |
| 2019/0387787 A1 | 12/2019 | Hejazi |
| 2020/0037664 A1 | 2/2020 | Fursa et al. |
| 2020/0060348 A1 | 2/2020 | Mironov et al. |
| 2020/0128878 A1 | 4/2020 | Stura et al. |
| 2020/0138098 A1 | 5/2020 | Mironov et al. |
| 2020/0163384 A1 | 5/2020 | Rossoll et al. |
| 2020/0163386 A1 | 5/2020 | Courbat et al. |
| 2020/0170300 A1 | 6/2020 | Gill |
| 2020/0229497 A1 | 7/2020 | Aoun et al. |
| 2020/0236999 A1 | 7/2020 | Mironov et al. |
| 2020/0329760 A1 | 10/2020 | Gonzalez Florez et al. |
| 2020/0367565 A1 | 11/2020 | Batista |
| 2021/0045455 A1 | 2/2021 | Davis et al. |
| 2021/0106046 A1 | 4/2021 | Courbat et al. |
| 2021/0137170 A1 | 5/2021 | Taurino et al. |
| 2021/0145057 A1 | 5/2021 | Reevell |
| 2021/0145061 A1 | 5/2021 | Fursa et al. |
| 2021/0145062 A1 | 5/2021 | Courbat et al. |
| 2021/0145071 A1 | 5/2021 | Butin et al. |
| 2021/0153547 A1 | 5/2021 | Thorens |
| 2021/0161208 A1 | 6/2021 | Mironov et al. |
| 2021/0204604 A1 | 7/2021 | Mironov et al. |
| 2021/0219617 A1 | 7/2021 | Lee et al. |
| 2021/0219618 A1 | 7/2021 | Fernando et al. |
| 2021/0251287 A1 | 8/2021 | Emmett et al. |
| 2021/0298360 A1 | 9/2021 | Acconcia et al. |
| 2021/0315278 A1 | 10/2021 | Fraser et al. |
| 2021/0329964 A1 | 10/2021 | Deforel et al. |
| 2021/0345659 A1 | 11/2021 | Arndt et al. |

(56) References Cited

U.S. PATENT DOCUMENTS

| | | |
|---|---|---|
| 2021/0345674 A1 | 11/2021 | Emmett et al. |
| 2022/0175040 A1 | 6/2022 | Spencer et al. |

FOREIGN PATENT DOCUMENTS

| | | |
|---|---|---|
| AU | 2015261887 A1 | 7/2016 |
| AU | 2015263436 A1 | 9/2016 |
| AU | 2015222843 A1 | 10/2016 |
| AU | 2016286401 A1 | 1/2018 |
| AU | 2017320216 A1 | 12/2018 |
| AU | 2017301985 A1 | 2/2019 |
| AU | 2018219468 A1 | 9/2019 |
| AU | 2019222811 A1 | 9/2019 |
| AU | 2019261824 A1 | 12/2019 |
| AU | 2019356134 A1 | 2/2021 |
| AU | 2019358424 A1 | 4/2021 |
| AU | 2020235790 A1 | 9/2021 |
| AU | 2020281604 A1 | 9/2021 |
| AU | 2020235315 A1 | 10/2021 |
| AU | 2020235462 A1 | 10/2021 |
| BR | 112019026139 A2 | 6/2020 |
| BR | 112021001594 A2 | 4/2021 |
| CA | 2937065 A1 | 11/2015 |
| CA | 2937719 A1 | 11/2015 |
| CA | 3014594 A1 | 8/2017 |
| CA | 3021251 A1 | 10/2017 |
| CA | 3014149 A1 | 12/2017 |
| CA | 3026992 A1 | 3/2018 |
| CA | 3032879 A1 | 5/2018 |
| CA | 3041012 A1 | 8/2018 |
| CA | 3074883 A1 | 3/2019 |
| CA | 3108453 A1 | 4/2020 |
| CA | 3111358 A1 | 4/2020 |
| CA | 3132230 A1 | 9/2020 |
| CA | 3132765 A1 | 9/2020 |
| CA | 3133067 A1 | 9/2020 |
| CA | 3132105 A1 | 12/2020 |
| CH | 707222 | 5/2014 |
| CN | 707222 | 10/2014 |
| CN | 104095291 | 10/2014 |
| CN | 104095291 A | 10/2014 |
| CN | 105263346 A | 1/2016 |
| CN | 105407750 A | 3/2016 |
| CN | 105764367 A | 7/2016 |
| CN | 106163309 A | 11/2016 |
| CN | 106455704 A | 2/2017 |
| CN | 106455715 A | 2/2017 |
| CN | 107708453 A | 2/2018 |
| CN | 108135276 A | 6/2018 |
| CN | 108135278 A | 6/2018 |
| CN | 108366629 A | 8/2018 |
| CN | 108471808 A | 8/2018 |
| CN | 108471813 A | 8/2018 |
| CN | 108697171 A | 10/2018 |
| CN | 109068741 A | 12/2018 |
| CN | 109195462 A | 1/2019 |
| CN | 109414067 A | 3/2019 |
| CN | 109496129 A | 3/2019 |
| CN | 109640716 A | 4/2019 |
| CN | 109890233 A | 6/2019 |
| CN | 109998171 | 7/2019 |
| CN | 110248561 A | 9/2019 |
| CN | 110545680 A | 12/2019 |
| CN | 110573035 A | 12/2019 |
| CN | 110621175 A | 12/2019 |
| CN | 110771258 A | 2/2020 |
| CN | 110799050 A | 2/2020 |
| CN | 110800372 A | 2/2020 |
| CN | 110891442 A | 3/2020 |
| CN | 110913712 A | 3/2020 |
| CN | 111031821 A | 4/2020 |
| CN | 111052858 A | 4/2020 |
| CN | 111107757 A | 5/2020 |
| CN | 111246761 A | 6/2020 |
| CN | 111902055 A | 11/2020 |
| CN | 112088577 A | 12/2020 |
| CN | 112153909 A | 12/2020 |
| CN | 112203539 A | 1/2021 |
| CN | 112367872 A | 2/2021 |
| CN | 112384091 A | 2/2021 |
| CN | 112638183 A | 4/2021 |
| CN | 112638186 A | 4/2021 |
| CN | 112739226 A | 4/2021 |
| CN | 112739227 A | 4/2021 |
| CN | 112739228 A | 4/2021 |
| CN | 112739229 A | 4/2021 |
| CN | 112804899 A | 5/2021 |
| CN | 112822950 A | 5/2021 |
| CN | 112911949 A | 6/2021 |
| CN | 113226084 A | 8/2021 |
| CN | 113329643 A | 8/2021 |
| CN | 113329644 A | 8/2021 |
| CN | 113423289 A | 9/2021 |
| CN | 113473871 A | 10/2021 |
| CN | 113557792 A | 10/2021 |
| CN | 113597263 A | 11/2021 |
| CN | 113613519 A | 11/2021 |
| CN | 113710113 A | 11/2021 |
| EA | 202090426 A1 | 7/2020 |
| EP | 0703735 A1 | 4/1996 |
| EP | 2975957 A1 | 1/2016 |
| EP | 2975958 A1 | 1/2016 |
| EP | 2994000 A1 | 3/2016 |
| EP | 2996504 A1 | 3/2016 |
| EP | 3076810 A1 | 10/2016 |
| EP | 3110270 A1 | 1/2017 |
| EP | 3145338 A1 | 3/2017 |
| EP | 3145341 A1 | 3/2017 |
| EP | 3145343 A1 | 3/2017 |
| EP | 3145344 A1 | 3/2017 |
| EP | 3183979 A1 | 6/2017 |
| EP | 3313213 A1 | 5/2018 |
| EP | 3337342 A1 | 6/2018 |
| EP | 3337343 A1 | 6/2018 |
| EP | 3364788 A1 | 8/2018 |
| EP | 3364793 A1 | 8/2018 |
| EP | 3370553 A1 | 9/2018 |
| EP | 3399876 A1 | 11/2018 |
| EP | 3405051 A1 | 11/2018 |
| EP | 3416507 A1 | 12/2018 |
| EP | 3426071 A1 | 1/2019 |
| EP | 3445186 A1 | 2/2019 |
| EP | 3462933 A1 | 4/2019 |
| EP | 3462934 A1 | 4/2019 |
| EP | 3462935 A1 | 4/2019 |
| EP | 3462936 A1 | 4/2019 |
| EP | 3490395 A1 | 6/2019 |
| EP | 3506771 A1 | 7/2019 |
| EP | 3541212 A1 | 9/2019 |
| EP | 3544452 A1 | 10/2019 |
| EP | 3579711 A1 | 12/2019 |
| EP | 3621465 A1 | 3/2020 |
| EP | 3629782 A1 | 4/2020 |
| EP | 3638058 A1 | 4/2020 |
| EP | 3646667 A1 | 5/2020 |
| EP | 3646669 A1 | 5/2020 |
| EP | 3646670 A1 | 5/2020 |
| EP | 3654790 A1 | 5/2020 |
| EP | 3664634 A1 | 6/2020 |
| EP | 3664642 A1 | 6/2020 |
| EP | 3664643 A1 | 6/2020 |
| EP | 3664644 A1 | 6/2020 |
| EP | 3679765 A1 | 7/2020 |
| EP | 3691479 A1 | 8/2020 |
| EP | 3695734 A1 | 8/2020 |
| EP | 3695735 A1 | 8/2020 |
| EP | 3760062 A1 | 1/2021 |
| EP | 3760063 A1 | 1/2021 |
| EP | 3760064 A1 | 1/2021 |
| EP | 3760065 A1 | 1/2021 |
| EP | 3772248 A1 | 2/2021 |
| EP | 3800966 A1 | 4/2021 |
| EP | 3801077 A1 | 4/2021 |
| EP | 3804461 A1 | 4/2021 |

(56) References Cited

FOREIGN PATENT DOCUMENTS

| | | |
|---|---|---|
| EP | 3806583 A1 | 4/2021 |
| EP | 3817607 A1 | 5/2021 |
| EP | 3818886 A1 | 5/2021 |
| EP | 3829356 A1 | 6/2021 |
| EP | 3829360 A1 | 6/2021 |
| EP | 3843570 A1 | 7/2021 |
| EP | 3855953 A1 | 8/2021 |
| EP | 3855954 A1 | 8/2021 |
| EP | 3855955 A1 | 8/2021 |
| EP | 3855956 A1 | 8/2021 |
| EP | 3855960 A1 | 8/2021 |
| EP | 3863432 A1 | 8/2021 |
| EP | 3863433 A1 | 8/2021 |
| EP | 3863449 A1 | 8/2021 |
| EP | 3900552 A1 | 10/2021 |
| EP | 3911187 A1 | 11/2021 |
| EP | 3915403 A1 | 12/2021 |
| EP | 3915404 A1 | 12/2021 |
| EP | 3915405 A1 | 12/2021 |
| IL | 272494 | 12/1899 |
| IL | 272894 | 12/1899 |
| IL | 278103 | 12/1899 |
| IL | 278583 | 12/1899 |
| IL | 278791 | 12/1899 |
| IL | 281654 | 12/1899 |
| IL | 281655 | 12/1899 |
| IL | 281656 | 12/1899 |
| IL | 281985 | 12/1899 |
| IL | 282015 | 12/1899 |
| IL | 282124 | 12/1899 |
| IL | 284470 | 12/1899 |
| IL | 286004 | 12/1899 |
| IL | 286027 | 12/1899 |
| IL | 286112 | 12/1899 |
| IL | 246477 A | 12/2019 |
| IN | 201617026912 | 12/1899 |
| IN | 201617026913 | 12/1899 |
| IN | 201817041404 | 12/1899 |
| IN | 201917004559 | 12/1899 |
| IN | 201917004916 | 12/1899 |
| IN | 201917034455 | 12/1899 |
| IN | 202117008016 | 12/1899 |
| IN | 202117013168 | 12/1899 |
| JP | 5986694 B1 | 12/1899 |
| JP | 6001201 B1 | 12/1899 |
| JP | 6077145 B2 | 12/1899 |
| JP | 6532067 B2 | 12/1899 |
| JP | 6535350 B2 | 12/1899 |
| JP | 6557660 B2 | 12/1899 |
| JP | 6629458 B2 | 12/1899 |
| JP | 6653260 B2 | 12/1899 |
| JP | 6666854 B2 | 12/1899 |
| JP | 6684720 B2 | 12/1899 |
| JP | 6714740 B2 | 12/1899 |
| JP | 6830126 B2 | 12/1899 |
| JP | 6866314 B2 | 12/1899 |
| JP | 6878684 B2 | 12/1899 |
| JP | 6882273 B2 | 12/1899 |
| JP | 6883029 B2 | 12/1899 |
| JP | 6898499 B2 | 12/1899 |
| JP | 6898500 B2 | 12/1899 |
| JP | 6911167 B2 | 12/1899 |
| JP | 6946328 B2 | 12/1899 |
| JP | 6949043 B2 | 12/1899 |
| JP | 03039077 | 2/2003 |
| JP | 2016528874 A | 9/2016 |
| JP | 2016214258 | 12/2016 |
| JP | 2019510469 A | 4/2019 |
| JP | 2019521657 A | 8/2019 |
| JP | 2019526247 A | 9/2019 |
| JP | 2019535283 A | 12/2019 |
| JP | 2020505077 A | 2/2020 |
| JP | 2020519266 A | 7/2020 |
| JP | 2020521439 A | 7/2020 |
| JP | 2020522998 A | 8/2020 |
| JP | 2020524982 A | 8/2020 |
| JP | 2020525014 A | 8/2020 |
| JP | 2020527338 A | 9/2020 |
| JP | 2020529217 A | 10/2020 |
| JP | 2020529218 A | 10/2020 |
| JP | 2020529842 A | 10/2020 |
| JP | 2020532314 A | 11/2020 |
| JP | 2020535797 A | 12/2020 |
| JP | 2021512627 A | 5/2021 |
| JP | 2021520219 A | 8/2021 |
| JP | 2021524257 A | 9/2021 |
| JP | 2021525540 A | 9/2021 |
| JP | 2021528953 A | 10/2021 |
| JP | 6967169 B1 | 11/2021 |
| JP | 2021532748 A | 12/2021 |
| JP | 2021532798 A | 12/2021 |
| KR | 101647936 B1 | 12/1899 |
| KR | 101648324 S1 | 12/1899 |
| KR | 102171229 B1 | 12/1899 |
| KR | 102278589 B1 | 12/1899 |
| KR | 102284091 B1 | 12/1899 |
| KR | 102323793 B1 | 12/1899 |
| KR | 102326187 B1 | 12/1899 |
| KR | 102326189 B1 | 12/1899 |
| KR | 1020170107518 | 12/1899 |
| KR | 20150143885 A | 12/2015 |
| KR | 1020170107518 | 9/2017 |
| KR | 20180135927 A | 12/2018 |
| KR | 20190011235 A | 2/2019 |
| KR | 20190039713 A | 4/2019 |
| KR | 20190084952 A | 7/2019 |
| KR | 20190141012 A | 12/2019 |
| KR | 20200011935 A | 2/2020 |
| KR | 20200019856 A | 2/2020 |
| KR | 20200024150 A | 3/2020 |
| KR | 20200031570 A | 3/2020 |
| KR | 20200038926 A | 4/2020 |
| KR | 20200040251 A | 4/2020 |
| KR | 20200069112 A | 6/2020 |
| KR | 20200078410 A | 7/2020 |
| KR | 20200092267 A | 8/2020 |
| KR | 20200134321 A | 12/2020 |
| KR | 20210014103 A | 2/2021 |
| KR | 20210014628 A | 2/2021 |
| KR | 20210018946 A | 2/2021 |
| KR | 20210027259 A | 3/2021 |
| KR | 20210035888 A | 4/2021 |
| KR | 20210047302 A | 4/2021 |
| KR | 20210061409 A | 5/2021 |
| KR | 20210064276 A | 6/2021 |
| KR | 20210064301 A | 6/2021 |
| KR | 20210064306 A | 6/2021 |
| KR | 20210064307 A | 6/2021 |
| KR | 20210070289 A | 6/2021 |
| KR | 20210070352 A | 6/2021 |
| KR | 20210075137 A | 6/2021 |
| KR | 20210099638 A | 8/2021 |
| KR | 20210132069 A | 11/2021 |
| KR | 20210132697 A | 11/2021 |
| KR | 20210134921 A | 11/2021 |
| KR | 20210134923 A | 11/2021 |
| KR | 20210135297 A | 11/2021 |
| KR | 20210136111 A | 11/2021 |
| RU | 2643421 C2 | 2/2018 |
| RU | 2665435 C1 | 8/2018 |
| RU | 2674612 C2 | 12/2018 |
| RU | 2709000 C2 | 12/2019 |
| RU | 2710773 C2 | 1/2020 |
| RU | 2736106 C1 | 11/2020 |
| RU | 2736745 C2 | 11/2020 |
| RU | 2737382 C2 | 11/2020 |
| RU | 2738701 C2 | 12/2020 |
| RU | 2746348 C2 | 4/2021 |
| RU | 2747537 C2 | 5/2021 |
| RU | 2019138679 A | 6/2021 |
| RU | 2751032 C2 | 7/2021 |
| RU | 2753568 C1 | 8/2021 |
| RU | 2760355 C2 | 11/2021 |
| TW | I669072 B | 12/1899 |

(56) References Cited

FOREIGN PATENT DOCUMENTS

| | | | |
|---|---|---|---|
| TW | I670017 B | 12/1899 | |
| TW | 201902372 A | 1/2019 | |
| TW | 202038780 A | 11/2020 | |
| WO | 9527411 A1 | 10/1995 | |
| WO | 2011063970 A1 | 6/2011 | |
| WO | WO2011063970 | 6/2011 | |
| WO | 2015019099 A1 | 2/2015 | |
| WO | WO 2015019099 | 2/2015 | |
| WO | WO2015019099 | 2/2015 | |
| WO | 2015070405 A1 | 5/2015 | |
| WO | WO 2015070405 | 5/2015 | |
| WO | 15177253 A1 | 11/2015 | |
| WO | 15177264 A1 | 11/2015 | |
| WO | 2017068093 | 10/2016 | |
| WO | 2017029268 A1 | 2/2017 | |
| WO | WO2017029268 | 2/2017 | |
| WO | 2017068094 A1 | 4/2017 | |
| WO | WO2017068093 | 4/2017 | |
| WO | WO 2017068094 | 4/2017 | |
| WO | 17085242 A1 | 5/2017 | |
| WO | WO2017072148 | 5/2017 | |
| WO | 2017108991 A1 | 6/2017 | |
| WO | WO 2017108991 | 6/2017 | |
| WO | 2017122196 A1 | 7/2017 | |
| WO | WO 2017122196 A1 | 7/2017 | |
| WO | 17141017 A1 | 8/2017 | |
| WO | 2017129617 A1 | 8/2017 | |
| WO | WO 2017129617 | 8/2017 | |
| WO | 2017072148 | 10/2017 | |
| WO | 2017178394 A1 | 10/2017 | |
| WO | WO 2017178394 | 10/2017 | |
| WO | 2017191176 A1 | 11/2017 | |
| WO | WO2017 0191176 | 11/2017 | |
| WO | 17207584 A1 | 12/2017 | |
| WO | 2017216671 | 12/2017 | |
| WO | 2017216671 A1 | 12/2017 | |
| WO | WO 2018002084 | 1/2018 | |
| WO | 18041450 A1 | 3/2018 | |
| WO | 18096000 A1 | 5/2018 | |
| WO | 18146071 A1 | 8/2018 | |
| WO | 2018162515 | 9/2018 | |
| WO | 18206616 A1 | 11/2018 | |
| WO | 18220558 A1 | 12/2018 | |
| WO | 19002329 A1 | 1/2019 | |
| WO | 19016740 A1 | 1/2019 | |
| WO | 19030364 A1 | 2/2019 | |
| WO | 2019149881 | 8/2019 | |
| WO | 2019149881 A1 | 8/2019 | |
| WO | 2019175810 | 9/2019 | |
| WO | 2019175810 A1 | 9/2019 | |
| WO | 19197170 A1 | 10/2019 | |
| WO | 19224380 A1 | 11/2019 | |
| WO | 19234582 A1 | 12/2019 | |
| WO | 20008008 A1 | 1/2020 | |
| WO | 2020011815 | 1/2020 | |
| WO | 2020011815 A2 | 1/2020 | |
| WO | 20025562 A1 | 2/2020 | |
| WO | 20025746 A1 | 2/2020 | |
| WO | 20044181 A1 | 3/2020 | |
| WO | 20064682 A1 | 4/2020 | |
| WO | 20064683 A1 | 4/2020 | |
| WO | 20064684 A1 | 4/2020 |
| WO | 20064685 A1 | 4/2020 |
| WO | 20064686 A1 | 4/2020 |
| WO | 20074494 A1 | 4/2020 |
| WO | 20074535 A1 | 4/2020 |
| WO | 20074622 A1 | 4/2020 |
| WO | 20116811 A1 | 6/2020 |
| WO | 20148214 A1 | 7/2020 |
| WO | 20153828 A1 | 7/2020 |
| WO | 20153829 A1 | 7/2020 |
| WO | 20153830 A1 | 7/2020 |
| WO | 20174026 A1 | 9/2020 |
| WO | 20174027 A1 | 9/2020 |
| WO | 20174028 A1 | 9/2020 |
| WO | 20174029 A1 | 9/2020 |
| WO | 20182735 A1 | 9/2020 |
| WO | 20182754 A1 | 9/2020 |
| WO | 20183165 A1 | 9/2020 |
| WO | 20229465 A1 | 11/2020 |
| WO | 20239597 A1 | 12/2020 |
| WO | 20245338 A1 | 12/2020 |
| WO | 20260883 A1 | 12/2020 |
| WO | 20260884 A1 | 12/2020 |
| WO | 20260885 A1 | 12/2020 |
| WO | 20260886 A1 | 12/2020 |
| WO | 21001267 A1 | 1/2021 |
| WO | 21001268 A1 | 1/2021 |
| WO | 21001511 A1 | 1/2021 |
| WO | 21001512 A1 | 1/2021 |
| WO | 21001548 A2 | 1/2021 |
| WO | 21001552 A1 | 1/2021 |
| WO | 21001566 A1 | 1/2021 |
| WO | 21037403 A1 | 3/2021 |
| WO | 21037655 A1 | 3/2021 |
| WO | 21074254 A1 | 4/2021 |
| WO | 21083986 A1 | 5/2021 |
| WO | 21105476 A1 | 6/2021 |
| WO | 21116241 A1 | 6/2021 |
| WO | 21140018 A1 | 7/2021 |
| WO | 21170640 A1 | 9/2021 |
| WO | 21170642 A1 | 9/2021 |
| WO | 21170649 A1 | 9/2021 |
| WO | 21170650 A1 | 9/2021 |
| WO | 21170651 A1 | 9/2021 |
| WO | 21170671 A1 | 9/2021 |
| WO | 21170672 A1 | 9/2021 |
| WO | 21170673 A1 | 9/2021 |
| WO | 21170675 A1 | 9/2021 |
| WO | 21170677 A1 | 9/2021 |
| WO | 21233914 A1 | 11/2021 |
| WO | 21233916 A1 | 11/2021 |
| WO | 21233918 A1 | 11/2021 |
| WO | 2022128585 | 6/2022 |

OTHER PUBLICATIONS

Patent Cooperation Treaty, "International Preliminary Report on Patentability," PCT/US2019/012204, dated Jul. 22, 2020, 7 pages.
Patent Cooperation Treaty, "Notification of Transmittal of the International Search Report and the Written Opinion of the International Search Authority of the Declaration," PCT/US22022/39794, dated Dec. 22, 2022, 22 pages.

* cited by examiner

HEAT-NOT-BURN DEVICE AND METHOD

CROSS-REFERENCE TO RELATED APPLICATION

This patent application is a continuation of U.S. patent application Ser. No. 16/022,482, filed Jun. 28, 2018, which claims the benefit of U.S. Provisional Patent Application Ser. No. 62/613,355, entitled "METHODS OF CONFORMING AND COATING A SUSCEPTOR TO EFFICIENTLY HEAT TOBACCO VIA AN INDUCTIVE PROCESS," filed Jan. 3, 2018, which applications are incorporated in their entirety here by this reference. 16022482

TECHNICAL FIELD

This invention relates to devices used as alternatives to conventional smoking products, such as electronic cigarettes, vaping systems, and in particular, heat-not-burn devices.

BACKGROUND

Heat-not-burn (HNB) devices heat tobacco at temperatures lower than those that cause combustion to create an inhalable aerosol containing nicotine and other tobacco constituents, which is then made available to the device's user. Unlike traditional cigarettes, the goal is not to burn the tobacco, but rather to heat the tobacco sufficiently to release the nicotine and other constituents through the production of aerosol. Igniting and burning the cigarette creates unwanted toxins that can be avoided using the HNB device. However, there is a fine balance between providing sufficient heat to effectively release the tobacco constituents aerosol form and not burn or ignite the tobacco. Current HNB devices have not found that balance, either heating the tobacco at temperatures that produce an inadequate amount of aerosol or over heating the tobacco and producing an unpleasant or "burnt" flavor profile. Additionally, the current methodology leaves traditional HNB device internal components dirtied with burning tobacco byproducts and the byproducts of accidental combustion.

For the foregoing reasons there is a need for an aerosol producing device that provides its user the ability to control the power of the device, which will affect the temperature at which the tobacco be heated via the inductive method to reduce the risk of combustion—even at what would otherwise be sufficient temperatures to ignite—while increasing the efficiency and flavor profile of the aerosol produced.

SUMMARY

The present invention is directed to a system and method by which a consumable tobacco component is quickly and incrementally heated by induction, so that it produces an aerosol that contains certain of its constituents but, not with the byproducts most often associated with combustion, for example, smoke, ash, tar and certain other potentially harmful chemicals. This invention involves positioning and incrementally advancing heat along a consumable tobacco component with the use of an induction heating element that provides an alternating electro-magnetic field around the component.

An object of the present invention is a device wherein induction heating source is provided for use to heat a consumable tobacco component.

Another object of the present invention is a consumable tobacco component comprised of several, sealed, individual, airtight, coated encasements containing a consumable tobacco preparation—and an induction heating source. The encasement may be an aluminum shell with pre-set openings. The encasements may be coated with a gel that seals the openings until an inductive heating process melts the gel, clearing the openings. In some embodiments, the gel can include a flavoring agent that can add flavor to or enhance the flavor of the tobacco aerosol.

In some embodiments, multiple encasements are stacked inside a paper tube with spaces between them, formed by excess aluminum wrapping at the bottom end of each encasement and channels on either side to allover for the aerosol produced. When the inductive heating source is activated, the pre-set openings are cleared, and flavor is combined with the aerosol to travel through the tube and be made available to the user of the device.

Using these methods and apparatus, the device is required to heat less mass, can heat-up immediately, cool down quickly and conserve power, allowing for greater use between re-charging sessions. This contrasts with the well-known, current, commercially available heat-not-burn devices.

Another object of the present invention is a tobacco-containing consumable component comprised of several, sealed, individual, airtight, coated encasements and an induction heating source. The encasements are then coated with a gel that seals them until an inductive heating process can melt the gel, clearing the openings. In some embodiments, the gel can include a flavoring agent that can add flavor to or enhance the flavor of the consumable tobacco component.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The invention of the present application is a device for generating aerosols from a consumable-containing product for inhalation in a manner that utilizes relatively high heat with minimal burning of the consumable-containing product. For the purposes of this application, the term "consumable" is to be interpreted broadly to encompass any type of pharmaceutical agent, drug, chemical compound, active agent, constituent, and the like, regardless of whether the consumable is used to treat a condition or disease, is for nutrition, is a supplement, or used for recreation. By way of example only, a consumable can include pharmaceuticals, nutritional supplements, over-the-counter medicants, tobacco, cannabis, and the like.

Figure 1:
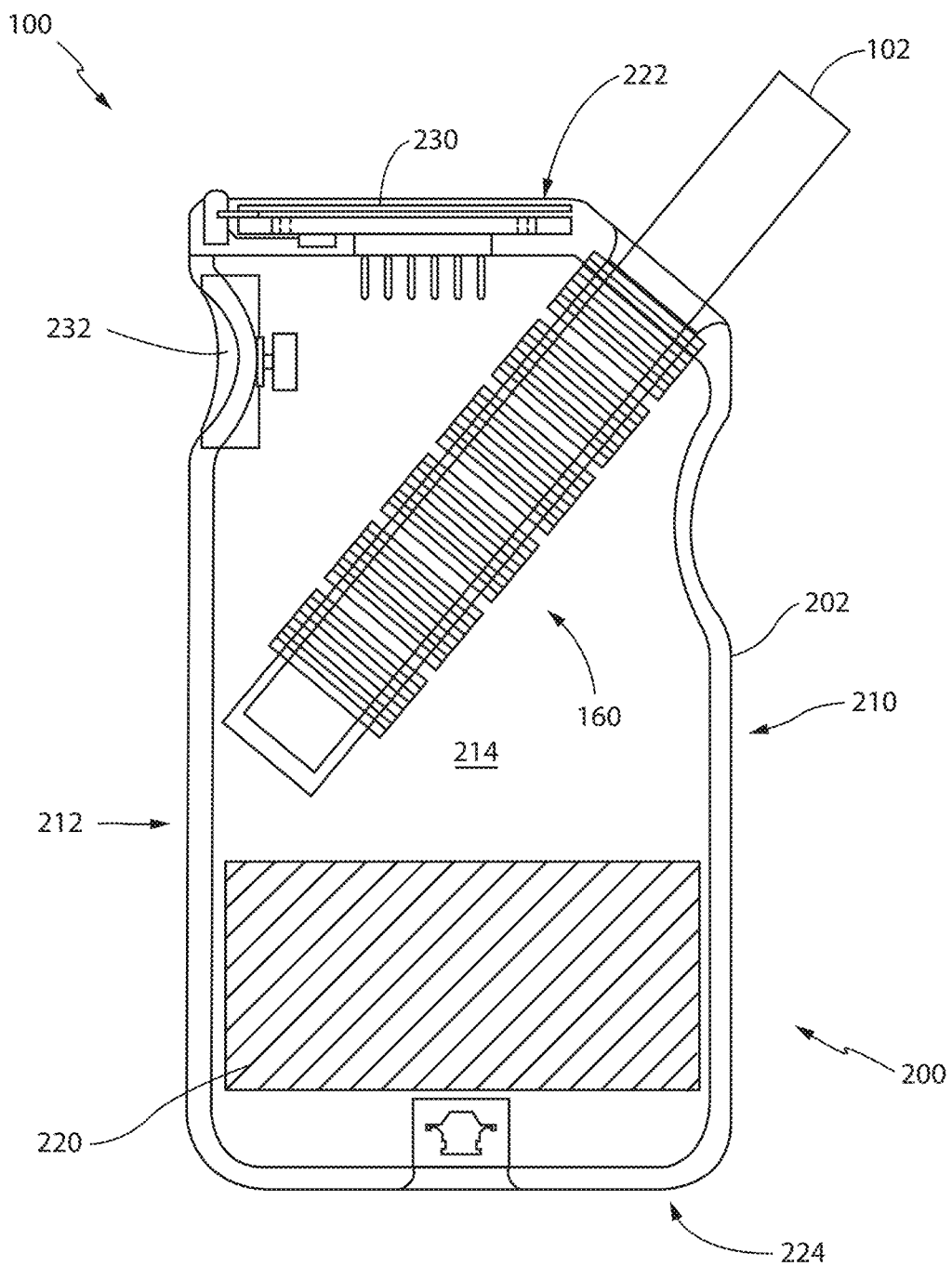
FIG. 1 shows a side view inside of an embodiment of the present invention.

With reference to FIG. 1, the device 100 comprises a consumable-containing package 102 and an aerosol producing device 200. The device 100 generates aerosols through a heat-not-burn process in which a consumable-containing unit 104 is heated to a temperature that does not burn the consumable-containing unit 104, but does release the consumable from the consumable-containing unit in the form of an aerosol product that can be inhaled. Thus, a consumable-containing unit 104 is any product that contains a consumable that can be released into aerosol form when heated to the proper temperature. The present application discusses application of the invention to a tobacco product to provide a concrete example. The invention, however, is not limited to use with tobacco products.

Consumable-Containing Package

With reference to FIGS. 2A-6B, the consumable-containing package 102 is the component that is heated to release the consumable in aerosol form. The consumable-containing package 102 comprises a consumable-containing unit 104, a metal (also referred to as the susceptor) 106 for heating the consumable-containing unit 104 through an inductive heating system, and an encasement 108 to contain the consumable-containing unit 104 and the susceptor 106. Flow well the consumable-containing package 102 is heated is dependent on product consistency. Product consistency takes into consideration various factors, such as the position, shape, orientation, composition, and other characteristics of the consumable-containing unit 104. Other characteristics of the consumable-containing unit 104 may include the amount of oxygen contained in the unit. The goal is to maximize product consistency by keeping each of these factors consistent in the manufacturing process.

If the term of the consumable-containing unit 104 is in direct physical contact the susceptor 106 with maximal contact area between each, then it can be inferred that the thermal energy induced in the susceptor 106 will be largely transferred to the consumable-containing unit 104. As such, the shape and arrangement of the consumable-containing unit 104 relative to the susceptor 106 is an important factor. In some embodiments, the consumable-containing unit 104 is generally cylindrical in shape. As such, the consumable-containing unit 104 may have a circular or oval-shaped cross-section.

In addition, another objective with respect to the design of the consumable-containing unit 104 is to minimize the amount of air to which the consumable-containing unit 104 is exposed. This eliminates or mitigates the risk of oxidation or combustion during storage or during the heating process. As a result, at certain settings, it is possible to heat the consumable-containing unit 104 to temperatures that would otherwise cause combustion when used with prior art devices that allow more air exposure.

As such, in the preferred embodiment, the consumable-containing unit 104 is made from a powdered form of the consumable that is compressed into a pellet or rod. Compression of the consumable reduces the oxygen trapped inside the consumable-containing unit 104. In some embodiments, the consumable-containing unit 104 may further comprise an additive, such as a humectant, flavorant, filler to displace oxygen, or vapor-generating substance, and the like. The additive may further assist with the absorption and transfer of the thermal energy as well as eliminating the oxygen from the consumable-containing unit 104. In an alternative embodiment, the consumable may be mixed with a substance that does not interfere with the function of the device, but displaces air in the interstitial spaces of the consumable and/or surrounds the consumable to isolate it from the air. In yet another alternative embodiment, the consumable could be formed into tiny pellets or other form that can be encapsulated to further reduce the air available to the consumable.

As shown in FIGS. 2A-2D, in the preferred embodiment, the consumable-containing unit 104 may be one elongated unit defining a longitudinal axis L. For example, the consumable-containing unit 104 may be an elongated cylinder or tube having a circular transverse cross-section or oval transverse cross-section. As such, the consumable-containing unit 104 may be defined by two opposing ends 105, 107 and a side fall 109 therebetween extending from the first end 105 to the second end 107 defining length of the consumable-containing 104.

The susceptor 106 may be similarly elongated and embedded in the consumable-containing unit 104, preferably, along the longitudinal axis L and extending substantially the length and width (i.e. the diameter) of the consumable-containing unit 104. In consumable-containing units 104 having an oval cross-section, the diameter refers to the major diameter defining the long axis of the oval.

Figure 2A:
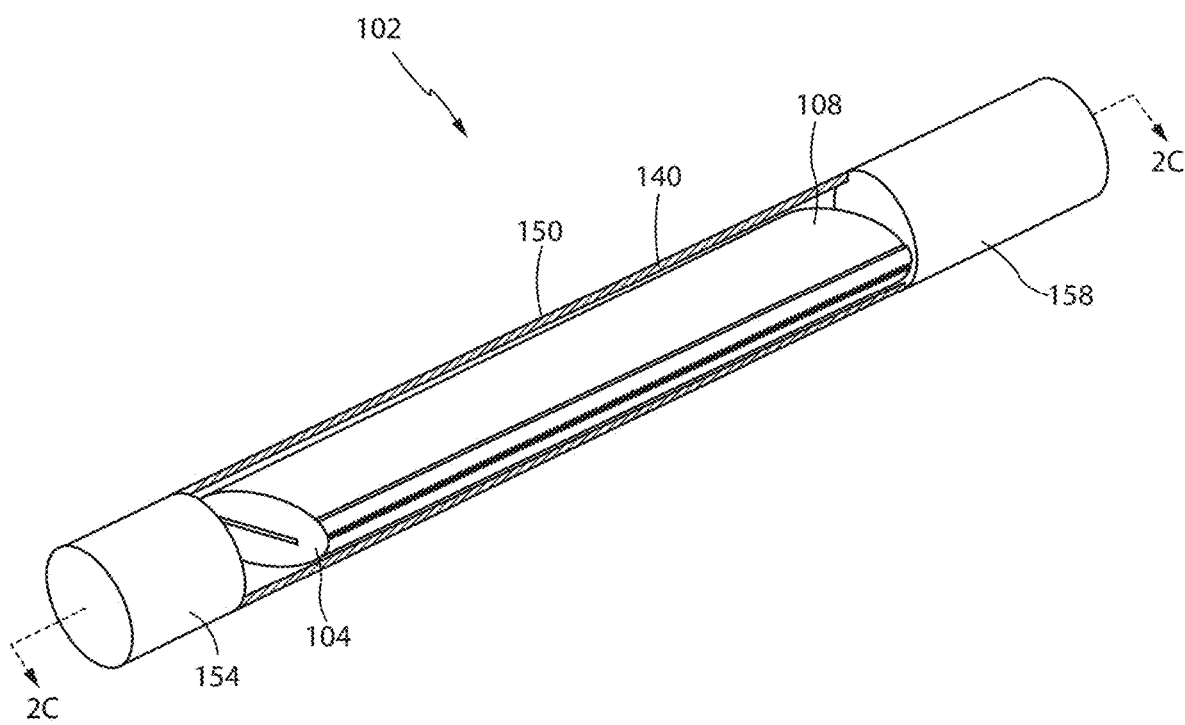
FIG. 2A shows a perspective view of an embodiment of the present invention with portions removed to show inside the embodiment.
Figure 2B:
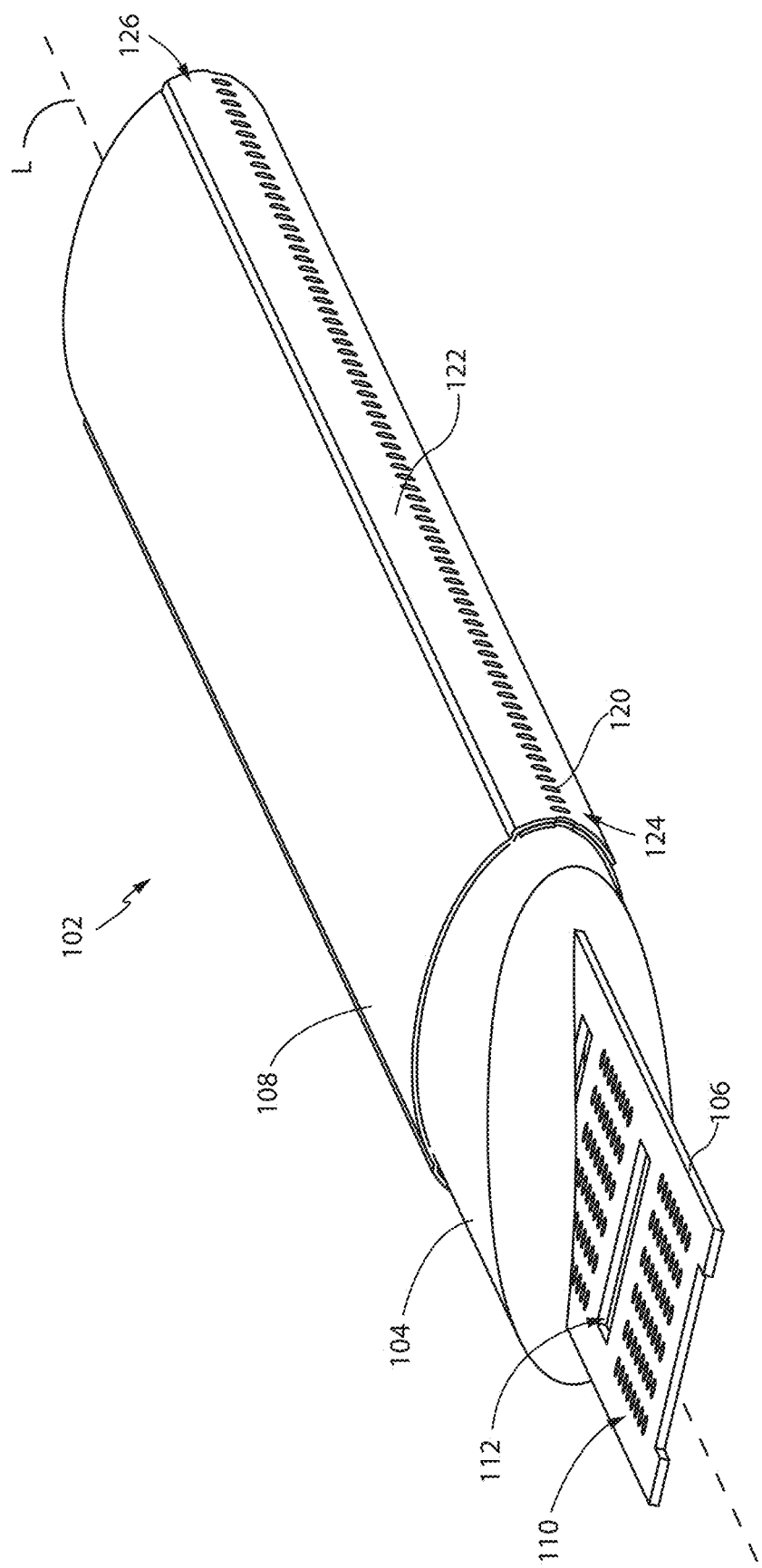
FIG. 2B shows a perspective view of the embodiment shown in FIG. 2A with portions cut away and/or removed to reveal internal components.
Figure 2C:
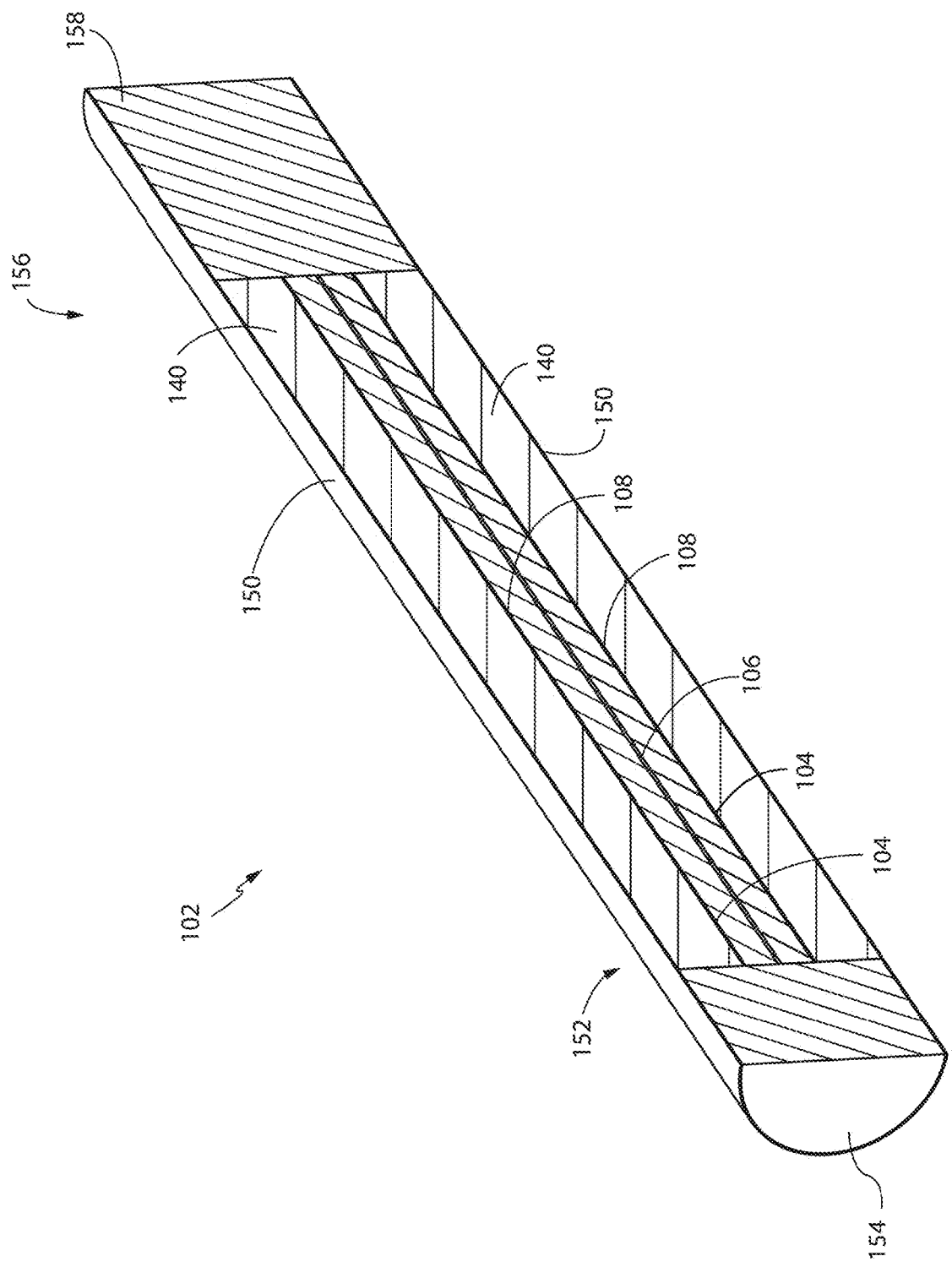
FIG. 2C shows a cross-sectional view of the embodiment shown in FIG. 2A cut along line 2C-2C.
Figure 2D:
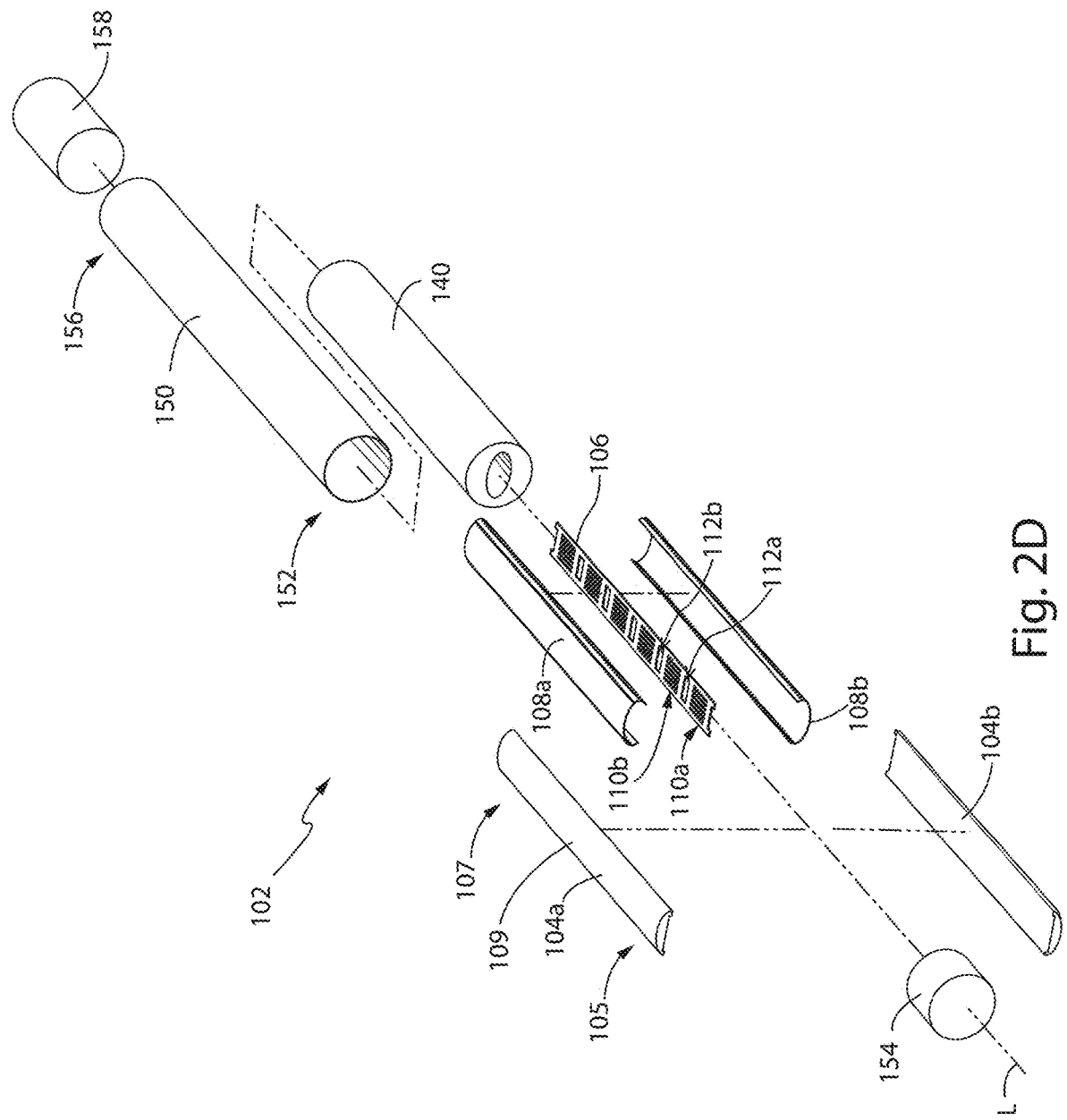
FIG. 2D shows an exploded view of the embodiment shown in FIG. 2A.
Figure 2E:
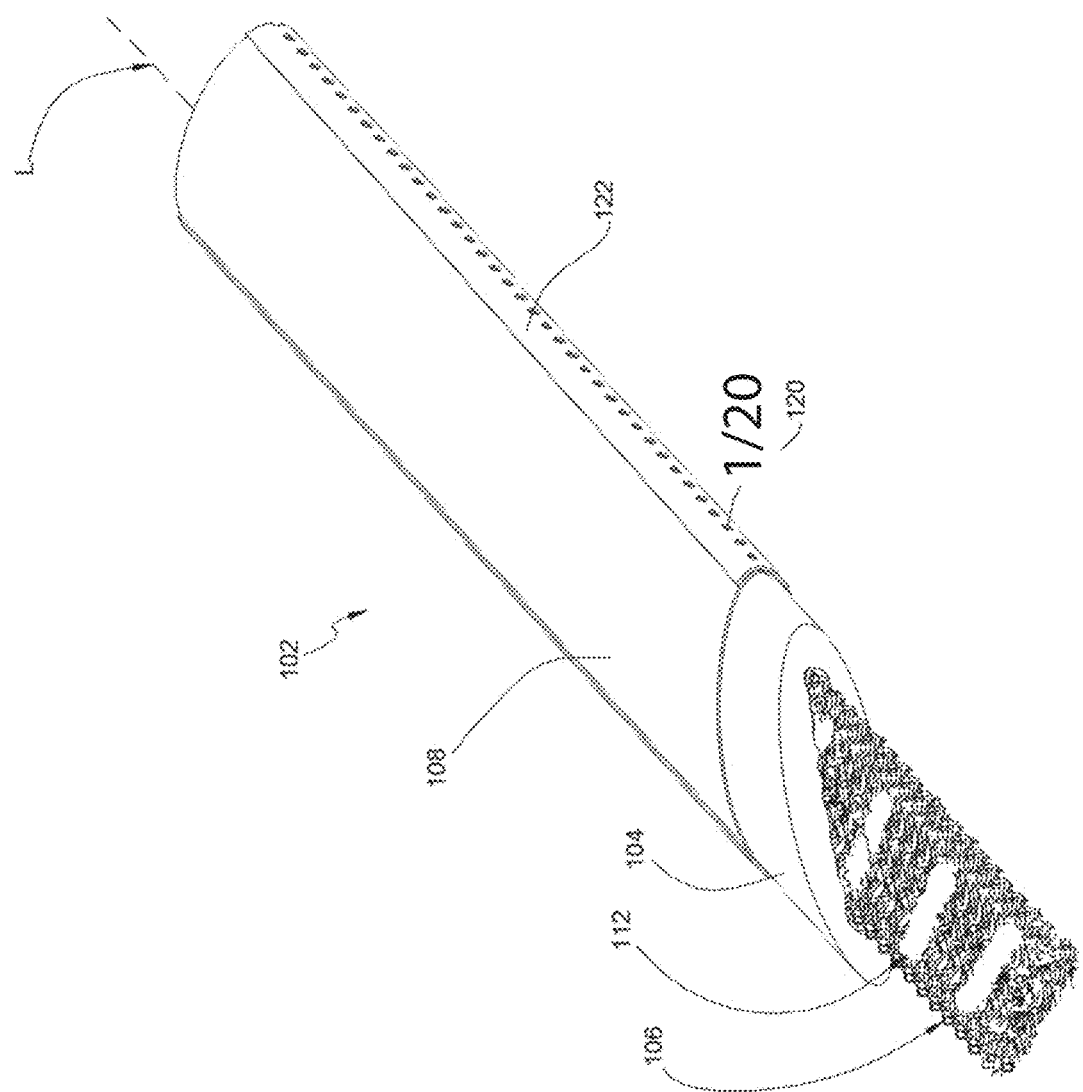
FIG. 2E shows a perspective view of another embodiment of the present invention with portions cut away and/or removed to reveal internal components.

The susceptor 106 can be machine extruded. Once extruded, the consumable-containing unit 104 can be compressed around the susceptor 106 along the length of the susceptor 106. Alternatively, the susceptor 106 could be stamped from flat metal stock or any other suitable method of fabrication prior to assembling the consumable containing unit 104 around the susceptor 106. In some embodiments, as shown in FIG. 2E, the susceptor 106 may be made of steel wool. For example, the susceptor 106 may be comprised of fine filaments of steel wool bundled together in the form of a pad. As such, the steel wool pad comprises numerous fine edges. In some embodiments, the steel wool pad may be doused with, immersed in, or fully filled with the additive, such as a humectant, flavorant, vapor-generating substance, a substance to retard oxidation of the steel wool (rust), and/or a filler to eliminate air between the steel wool filaments, and the like. As shown in FIG. 2E, there may be cut-outs along the steel wool pad to divide the consumable containing unit 104 into discrete segments for individual heating, as described below. Alternatively, individual pads of steel wool may be used, separated by space and/or consumable, so that each pad may be heated individually during use.

Advantages of the steel wool, include, but are not limited to, easy disposability from an environmental standpoint in that it begins to oxidize soon after it is heated; and thereby, becomes friable and degrades easily without dangerous sharp edges. Being composed of iron and carbon it is relatively non-toxic.

The susceptor 106 can be made of any metal material that generates heat when exposed to varying magnetic fields as in the case of induction heating. Preferably, the metal comprises a ferrous metal. To maximize efficient heating of the consumable-containing unit 104, the susceptor 106 generally matches the shape of the largest cross-sectional area of the consumable-containing unit 104 so as to maximize the surface area with which the consumable-containing unit 104 comes into contact with the susceptor 106, but other configurations may also be used. In the embodiments in which the consumable-containing unit 104 is an elongated cylinder, the largest cross-sectional area would be defined by dividing the elongated cylinder down the longitudinal axis L along its major diameter creating a rectangular cross-sectional area. As such, the susceptor 106 would also be rectangular with dimensions substantially similar to the dimensions of the cross-sectional area of the elongated cylinder.

In some embodiments, the susceptor 106 may be a metal plate. In some embodiments, the susceptor 106 may be a metal plate with a plurality of openings 110, like a mesh screen. Inductive heating appears to be most effective and efficient at the edges of the susceptor 106. A mesh screen creates more edges in the susceptor 106 that can contact the consumable-containing unit 104 because the edges define the openings 110.

Preferably, the susceptor 106 may be a strip patterned with an array of small openings 110 to increase the amount of edges that can be utilized in an efficient inductive heating process, followed by a larger gap 112 that allows for that length of the susceptor 106 that will not allow for inductive heating, or at least mitigate inductive heating and/or mitigate conduction from the segment being heated. This configuration allows for the consumable-containing package 102 to be heated in discrete segments. The elongated susceptor 106 may be an elongated metal plate having a longitudinal direction, the elongated metal plate comprising sets of openings 110a, 110b and sets of gaps 112a, 112b wherein the sets of openings 110a, 110b alternate in series with the sets of gaps 112a, 112b along the longitudinal direction of the elongated metal plate such that each set of openings 110a, 110b is adjacent to one of the gaps 112a, 112b. Therefore, moving from one end of the susceptor 106 to the opposite end, there is a first set of openings 110a, then a first gap 112a, then a second set of openings 110b, then a second gap 112b, and so on. In the area of the gaps 112, there is very little metal material; therefore, there is minimal heat transfer. As such, even though the consumable-containing unit 104 is a single unit, it can still be heated in discrete sections. The consumable-containing unit 104 and susceptor 106 are then wrapped in an encasement 108.

In the preferred embodiment, the encasement 108 may be made of aluminum with pre-punched openings 120. The consumable-containing unit 104 is placed inside the encasement 108 to contain the heat generated by the susceptor 106. The openings 120 in the encasement 108 allow the consumable aerosol to escape when heated. Because the openings 120 create an avenue through which air can enter into the encasement 108 to be exposed to the consumable-containing unit 104, the openings 120 may be temporarily sealed using a coating. The coating is preferably made of a composition that melts at temperatures that create consumable aerosols. Therefore, as the susceptor 106 is heated, due to the lack of air inside the encasement 108, the consumable-containing unit 104 can be raised to exceedingly high temperatures without combusting. As the susceptor 106 reaches high temperatures, the consumable aerosols that begin to form, are not able to escape. When the coating melts away and exposes the opening 120, then the consumable aerosols are able to escape the encasement 108 for inhalation. In the preferred embodiment, the coating may be propylene glycol alginate ("PGA") gel. The coating may also include a flavoring. Therefore, as the coating melts away and the consumable aerosol is released, the flavoring is also released with the consumable aerosol. In some embodiments, the flavoring can be mixed with the additive.

In some embodiments, the openings 120 may be a plurality of holes or slits. The openings 120 may be formed along the length of the sidewall 122 of the encasement 108, arranged radially around the sidewall 122, arranged randomly or uniformly throughout the sidewall 122, and the like. In some embodiments, the openings 120 may be a plurality of holes along the opposite ends 124, 126 of the encasement 108. In some embodiments with the elongated consumable-containing unit 104, the encasement 108 may also be elongated with the opening 120 in the form of one or more elongated slits traversing the length of the encasement parallel to the longitudinal axis L, thereby creating a seam. That seam may be folded or crimped, but still leave a gap through which consumable aerosols may travel, either along its entire length or in discrete areas. Like the openings 120 described above, the seam may be sealed with a coating.

The consumable-containing package 102 may further comprise a filter tube 140 to encapsulate the consumable-containing unit 104, susceptor 106, and the encasement 108. The filter tube 140 may be made of filter material to capture any unwanted debris while allowing the consumable aerosol that is released from the heating of the encasement to pass transversely through the filter. The filter tube 140 may surround the encasement 108 and further cover the coated openings 120. Because the filter tube 140 may be made of filtering material, the consumable aerosol is able to travel through the filter tube 140. By way of example only, the filter tube may be made of cellulose or cellulose acetate, although any suitable filter material may be used.

The consumable-containing package 102 may further comprise a housing 150 to enclose the filter tube 140. The housing 150 may be a paper tube. The housing 150 is less likely to allow the consumable aerosols to pass through. As such, the housing 150 wrapped around the filter tube 140 creates a longitudinal channel through the filter tube 140 through which the consumable aerosol travels, rather than escaping radially out the filter tube 140. This allows the consumable aerosol to follow the path of inhalation towards the user's mouth. One end 152 of the housing 150 may be capped with an end cap 154. The end cap 154 may be comprised of a type of filter material. At the opposite end 156 of the housing 150 is a mouthpiece 158 that the user sucks on to draw the heated consumable aerosol out of the encasement 108 along the filter tube 140 towards the mouthpiece 158 and into the user's mouth. As such, the mouthpiece 158 may also be a type of filter, similar to that of the end cap 154. Where the consumable containing package 102 includes a channel through which the consumable aerosol travels, and that channel leads directly to the mouthpiece 158 that is also part of the consumable containing package 102, and the channel is isolated from the case 202, the case 202 will remain free of any residue or byproducts formed during operation of the device. In this configuration, the case 202 stays clean and does not require the user to periodically clean out the case 202.

In some embodiments, the encasements 108 may be made of a two piece unit having a first encasement section 108a and a second encasement section 108b. The consumable-containing unit 104 can be inserted into the first encasement section 108a and the second encasement section 108b may be placed on top of the first encasement section 108a to cover the consumable-containing unit 104. Preset openings 120 can be formed into the encasement 108 prior to encapsulating the consumable-containing unit 104.

Having established the general principles of the consumable-containing package 102, variations have also been contemplated that achieve the same objectives. For example, in some embodiments, the consumable-containing unit 104 may comprise two elongated sections 104a, 104b. The two elongated sections 104a, 104b of the consumable-containing unit 104 may be defined by a plane parallel to and cutting through the longitudinal axis L along the diameter. Therefore, the two elongated sections 104a, 104b may be half-cylinder sections that when mated together form a full cylindrical consumable-containing unit 104.

In some embodiments, as shown in FIGS. 3A-3D, the consumable-containing unit 104 may be in the form of pellet or tablet. Unlike the consumable-containing unit 104 that is an elongated cylinder or tube in which the length of the sidewall 109 is much longer than the diameter, in the tablet embodiment, the tablet may be a short cylinder defining a longitudinal axis L, wherein the length of the sidewall 109 is closer to the size of the diameter, or shorter than the diameter. The susceptor 106 may have a flat, circular shape to match the cross-sectional shape of the tablet when cut transversely, perpendicular to the longitudinal axis L. The consumable-containing unit 104 can be compressed about the susceptor 106. To mimic a cigarette, a plurality of the consumable-containing units 104 can be stacked, end-to-end along their longitudinal axes L, to form an elongated cylinder. Therefore, each individual consumable-containing unit 104 can be heated separately, effectively mimicking the segments of the consumable-containing unit 104 having an elongated, tubular body.

Other shapes can also be used, such as square or rectangular with a susceptor 106 having a corresponding shape. The cylindrical shape, however, is preferred because of the ease with which such shape can be used to is the shape of an actual cigarette.

Figure 4A:
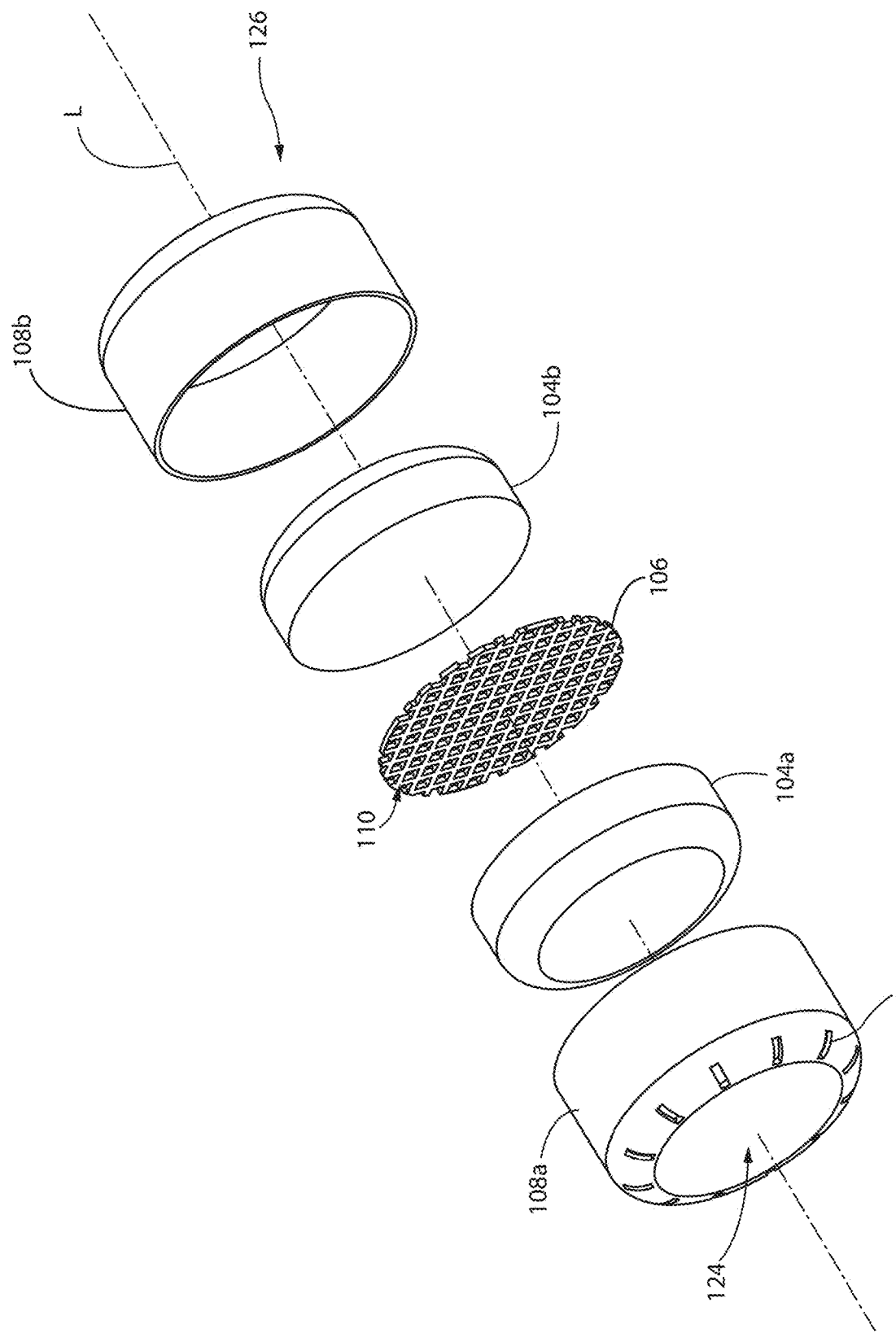
FIGS. 4A and 4B show an exploded views of embodiments of a consumable-containing unit.
Figure 4B:
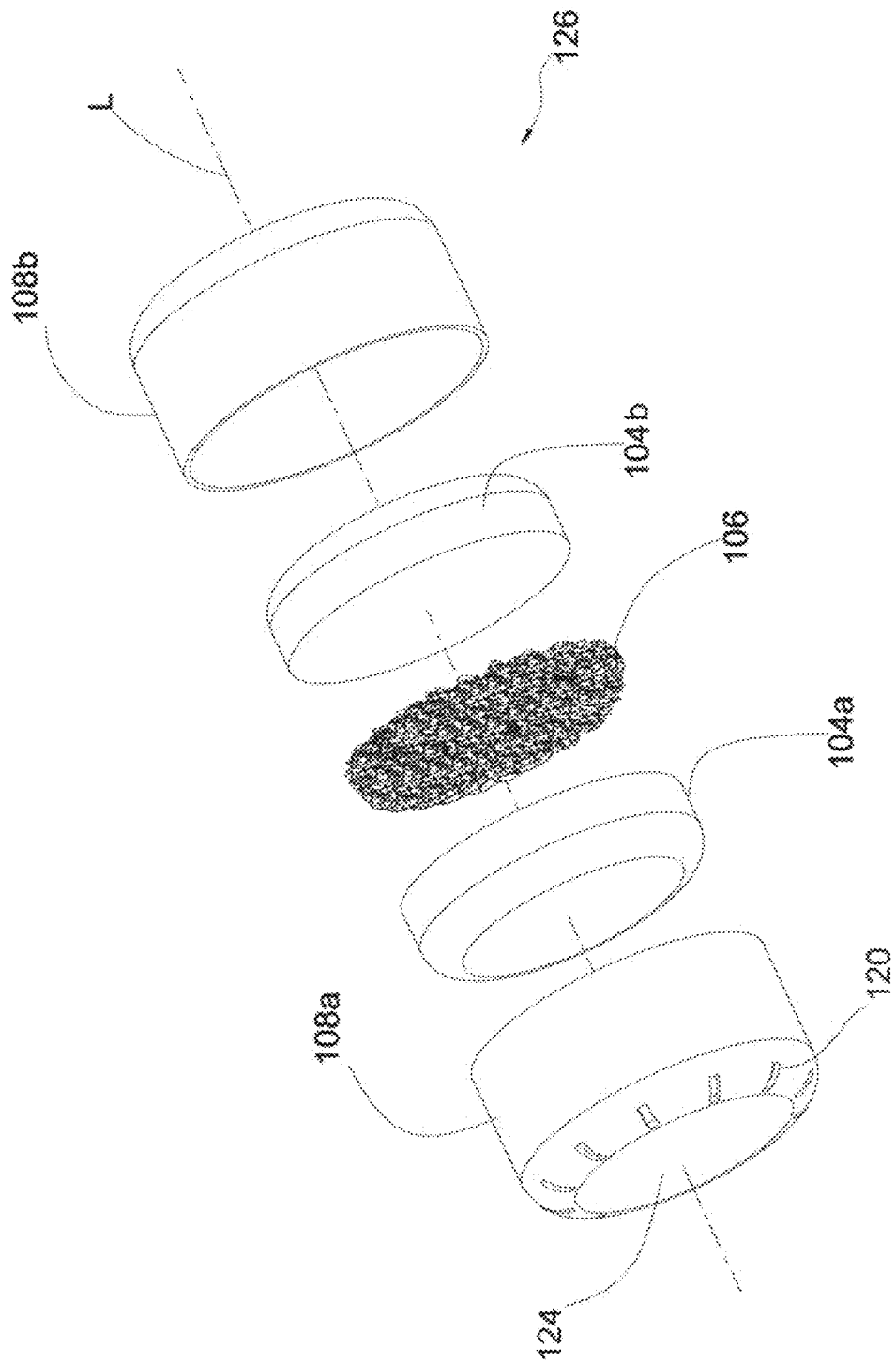
Figure 5A:
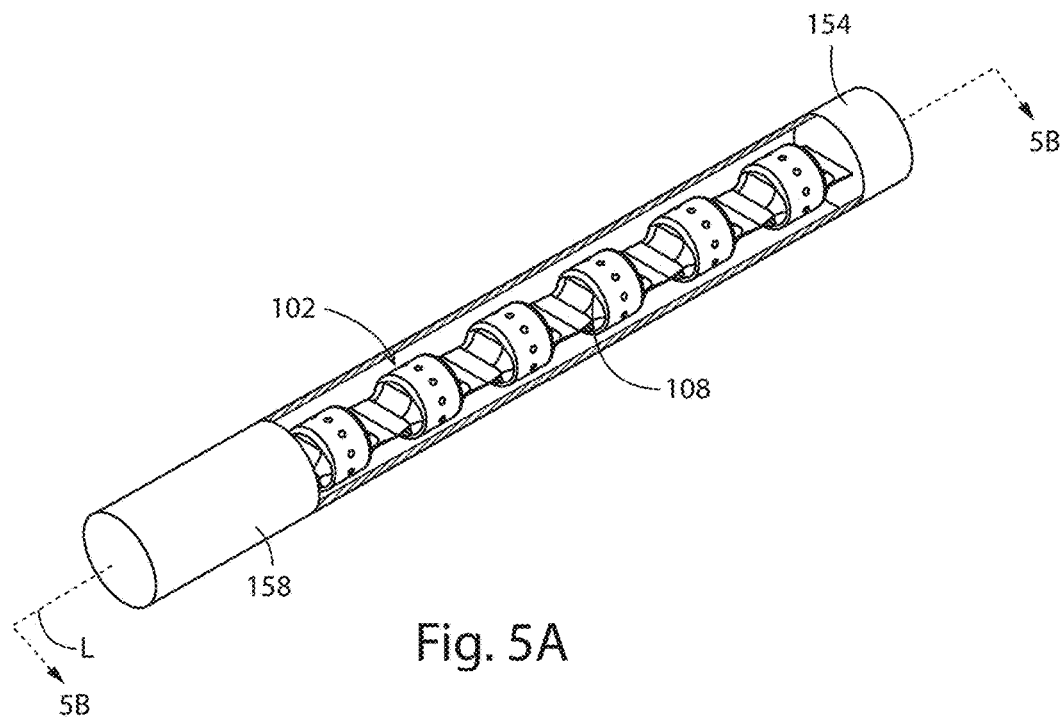
FIG. 5A shows a perspective view of another embodiment of the present invention.
Figure 5B:
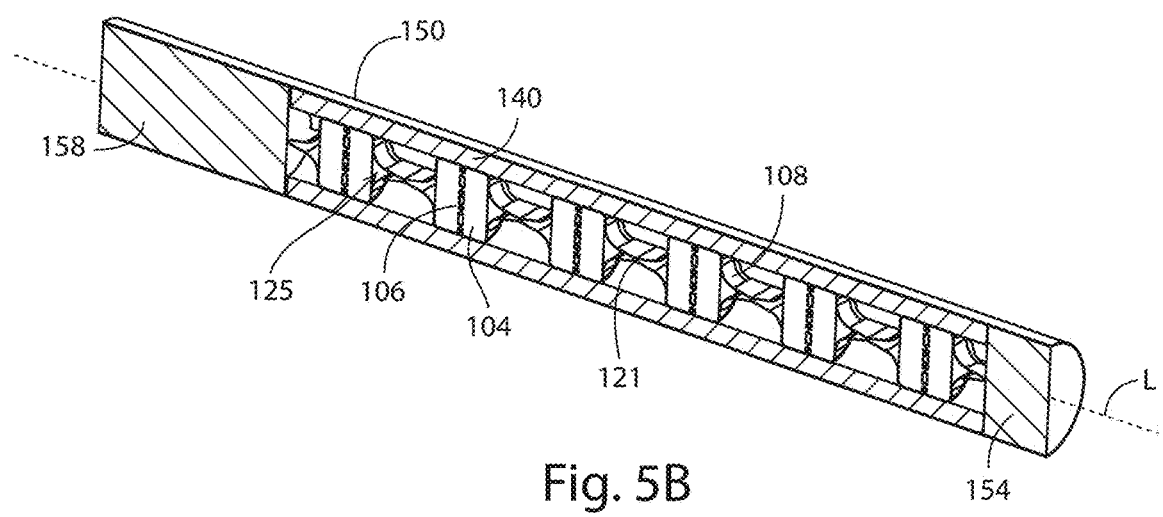
FIG. 5B shows a cross-sectional view of the embodiment shown in FIG. 5A taken along line 5B-5B.
Figure 5C:
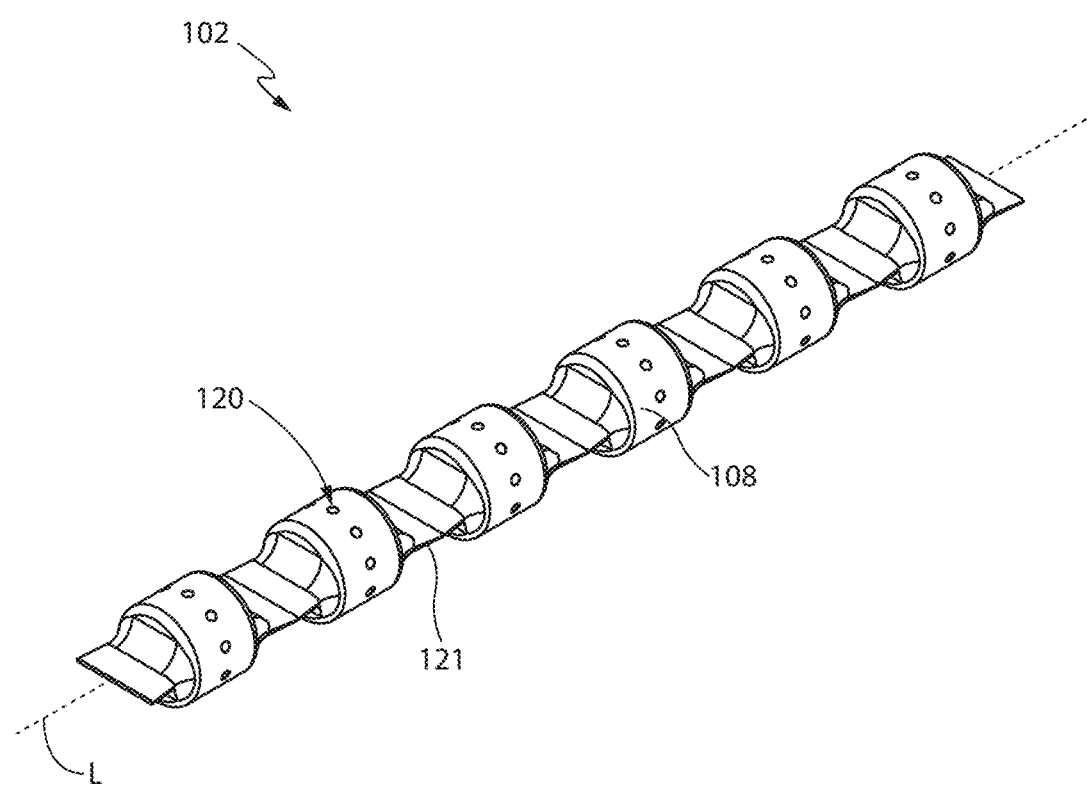
FIG. 5C shows a perspective view of a consumable-containing package from the embodiment shown in FIG. 5A.

In some embodiments, the consumable-containing unit 104 may be formed from two sections 104a, 104b of the consumable-containing unit 104 combined together to make a whole, as shown in FIGS. 4A and 4B. The two sections 104a, 104b are defined by splitting the consumable-containing unit 104 in half transversely along a plane perpendicular to the longitudinal axis L. The susceptor 106 may be sandwiched in between the two sections 104a, 104b. With the susceptor 106 sandwiched in between the two consumable-containing sections 104a, 104b, the consumable-containing unit 104 can be enclosed by the encasement 108. This process can be repeated to create a plurality of individual consumable-containing units 104 sandwiching respective susceptors 106, each individually contained in a respective encasement 108. The plurality of consumable-containing units 104 may be stacked, one on top of the other to create the consumable-containing package 102 in which each individual consumable-containing unit 104 may be heated individually, one at a time.

Figure 3A:
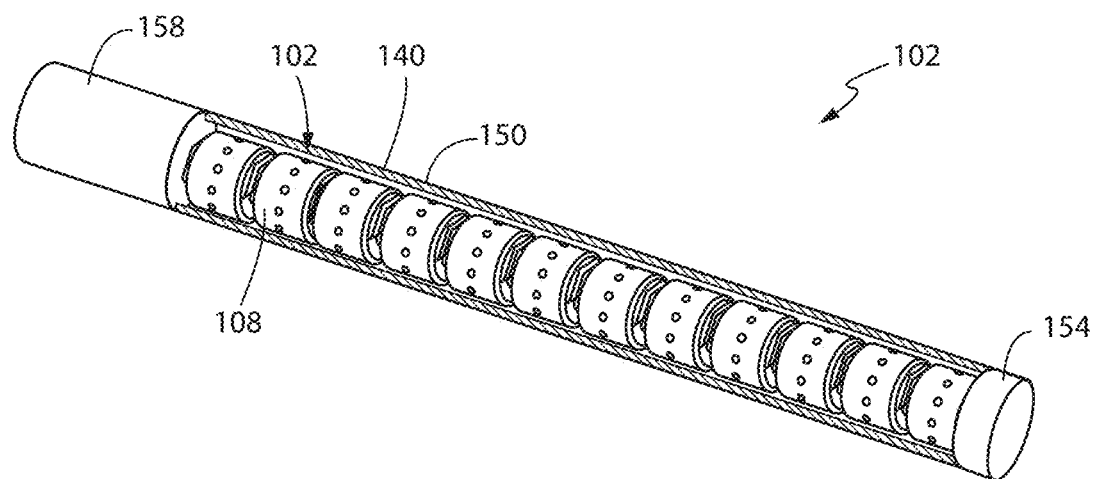
FIG. 3A shows a perspective view of another embodiment of the present invention.
Figure 3B:
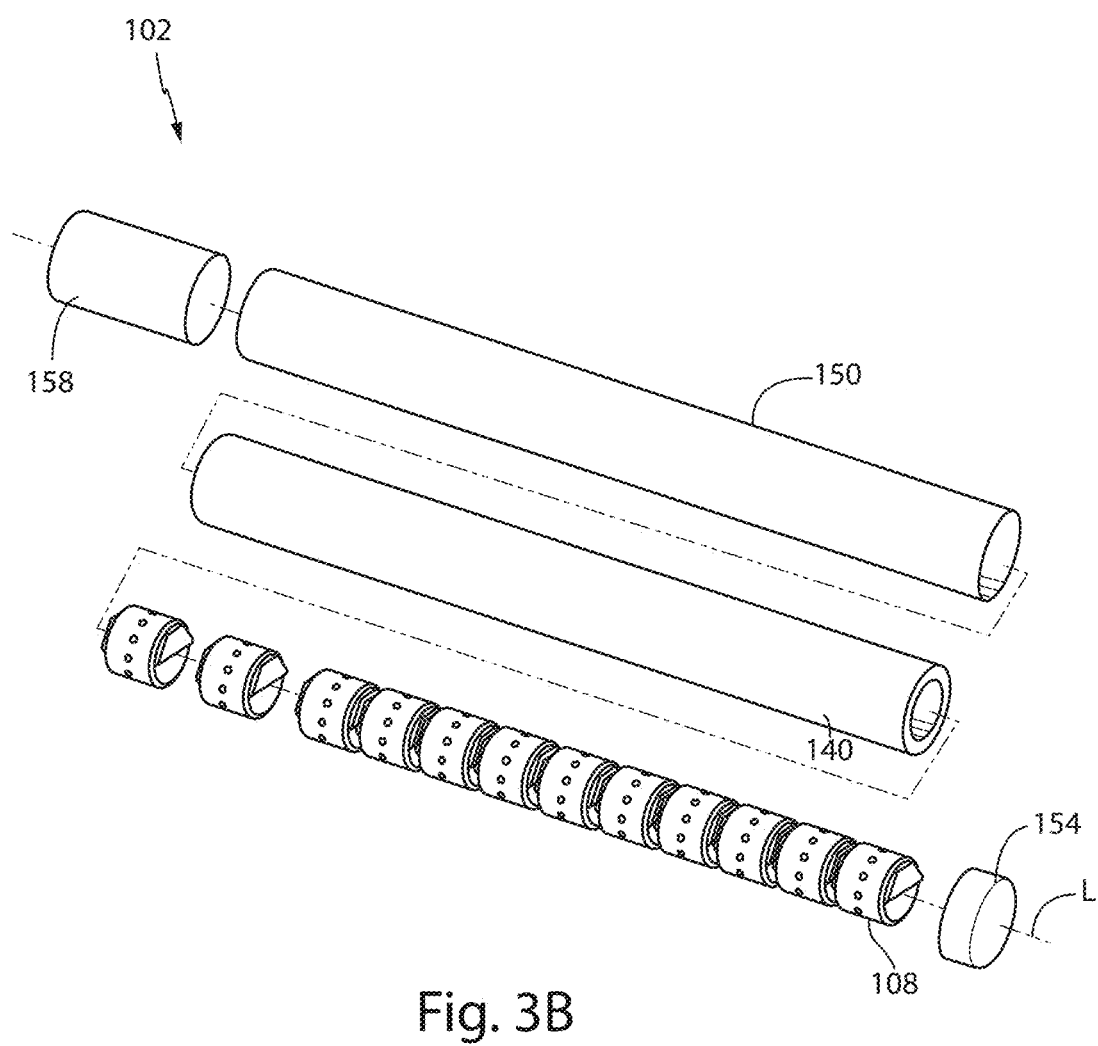
FIG. 3B shows a partially exploded view of the embodiment shown in FIG. 3A.
Figure 3C:
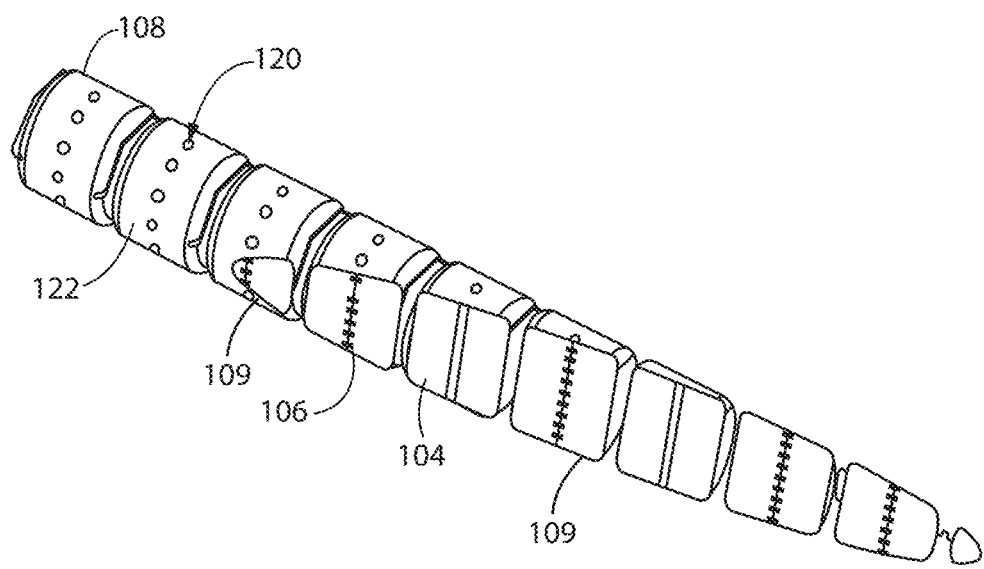
FIG. 3C shows a perspective view of the embodiment shown in FIG. 3A with portions cut away and/or removed to reveal internal components.
Figure 3D:
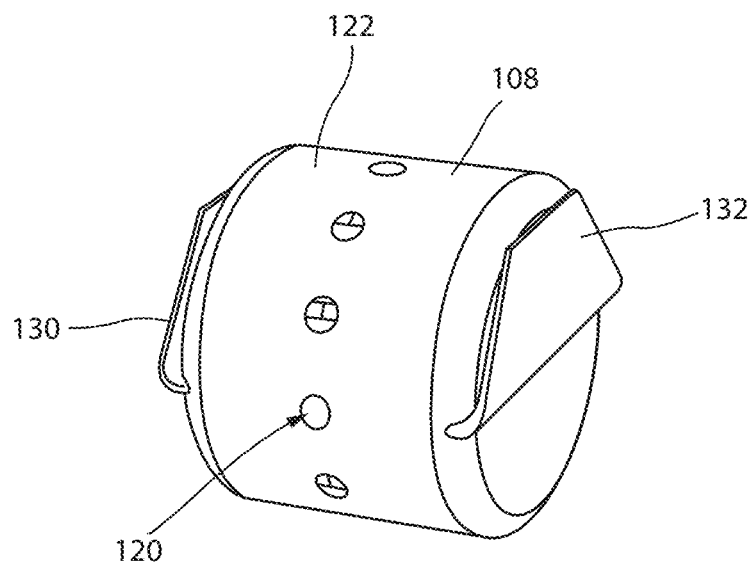
FIG. 3D shows a close-up, perspective view of a consumable-containing unit shown in FIG. 3A.

In some embodiments, the encasement 108 may be aluminum wrapped around a consumable-containing unit 104. The aluminum can have excess folds 130, 132 at opposite ends as shown in FIG. 3D. These excess folds 130, 132 create a gap in between adjacent consumable-containing units 104 when stacked on top of each other.

In some embodiments, the encasement 108 may be two-pieces having a first encasement section 108a and a second encasement section 108b that serves as a covering or cap to enclose the consumable-containing unit 104 inside the first encasement section 108a, as shown in FIGS. 4A and 4B. As described previously, the openings 120 on the encasement 108 may be along the sidewall 122 or at the ends 124, 126. As described previously, the susceptor 106 may be any type of metal that is subject to induced heating, including steel wool as shown in FIG. 4B. In the preferred embodiments, numerous edges are created in the susceptor 106 by creating a plurality of holes 110 or using steel wool filaments compressed together. The steel wool filaments may be fine to medium grade. As discussed above, the steel wool pad may be soaked in, coated, or filled with additive, flavorant, protectant, and/or filler.

Figure 6A:
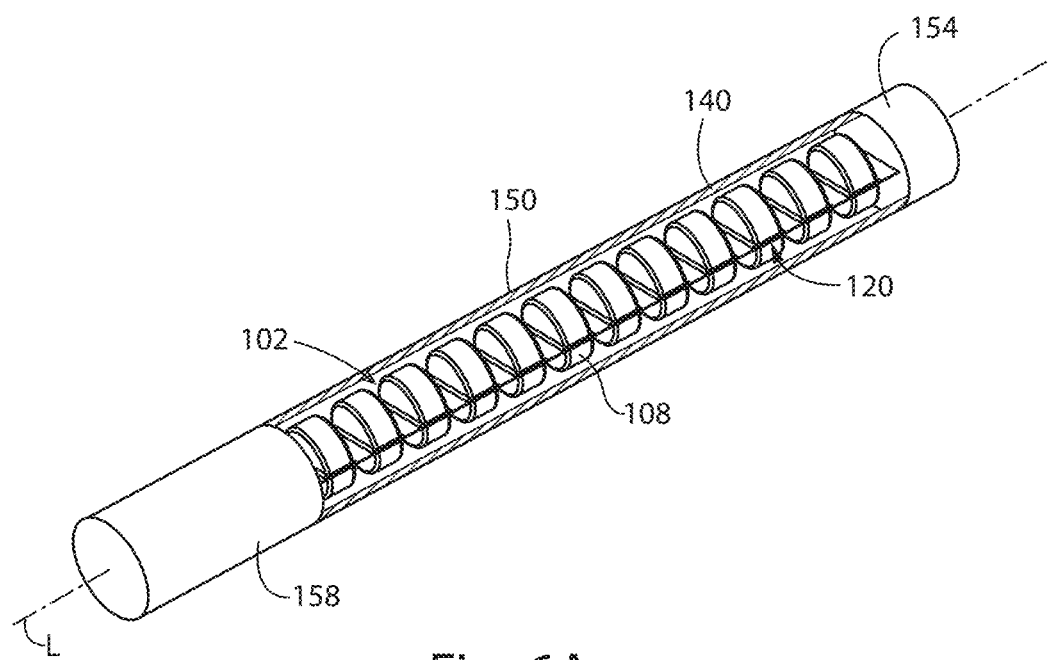
FIG. 6A shows a perspective view of another embodiment of the present invention.
Figure 6B:
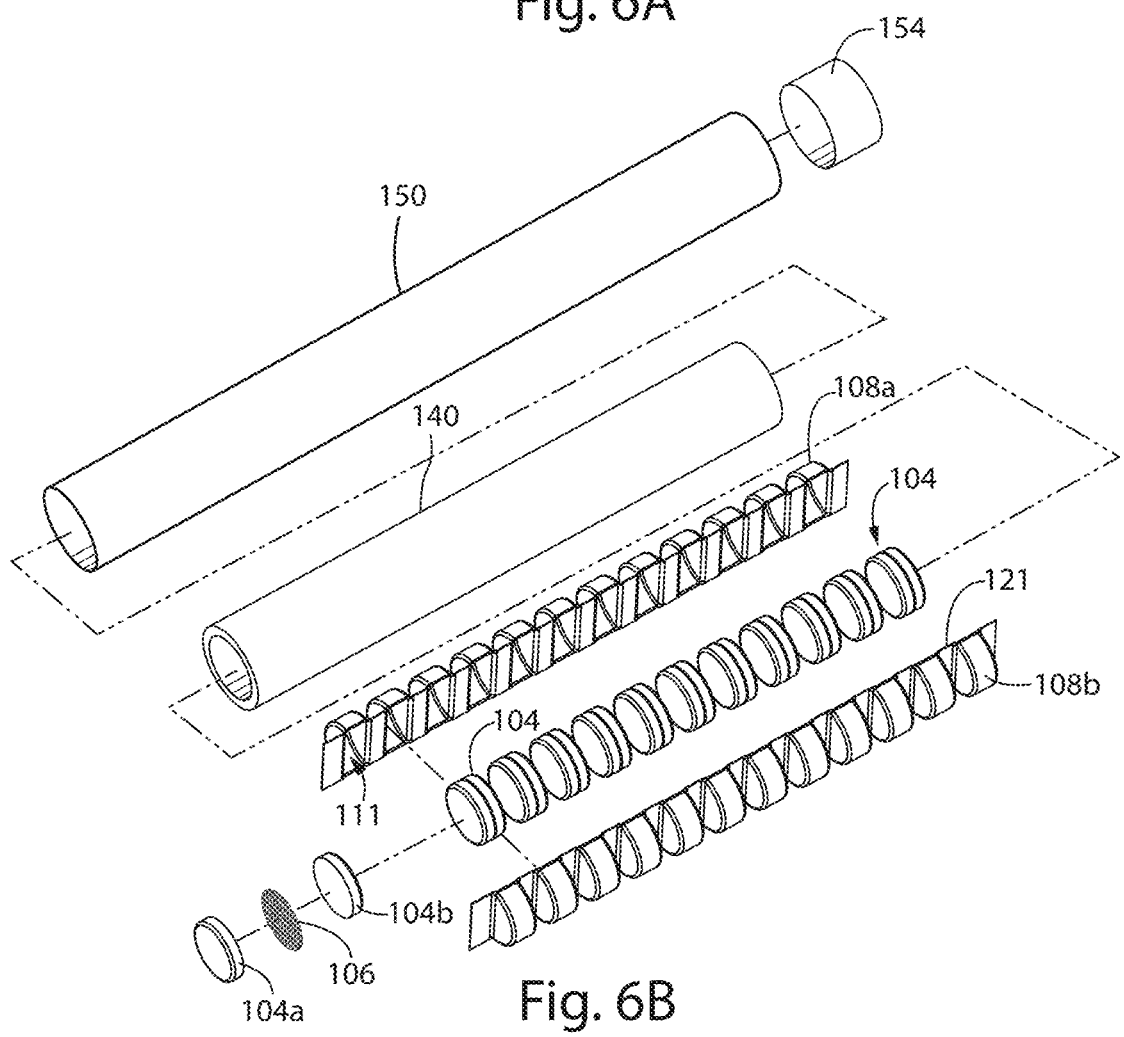
FIG. 6B shows an exploded view of the embodiment shown in FIG. 6A.

In some embodiments, a plurality of consumable-containing units 104 may be contained in a single elongated encasement 108, as shown in FIGS. 5A-6B. The encasement 108 may be molded with compartments 111 to receive each individual consumable-containing unit 104. In some embodiments, the individual compartments 111 may be connected to each other by a bridge 121. In some embodiments, the bridge 121 may define a channel 125 that allows fluid communication from one compartment 111 to another. In some embodiments, the bridge 121 may be crimped to prevent fluid communication between one compartment 111 and the other through the bridge 121. In some embodiments, the elongated encasement 108 may be a two-piece assembly split transversely along the longitudinal axis L, as shown in FIGS. 6A-6B. The consumable-containing units 104 can be seated in the compartments 111 of one of the encasement sections 108a. The second encasement section 108b can then be mated to the first encasement section 108*a* to cover the consumable-containing units 104. The split between the first encasement section 108*a* and the second encasement section 108*b* can be used as the opening 120. Alternatively, preset openings 120 can be formed in one or both of the encasement sections 108*a*, 108*b*.

Figure 7A:
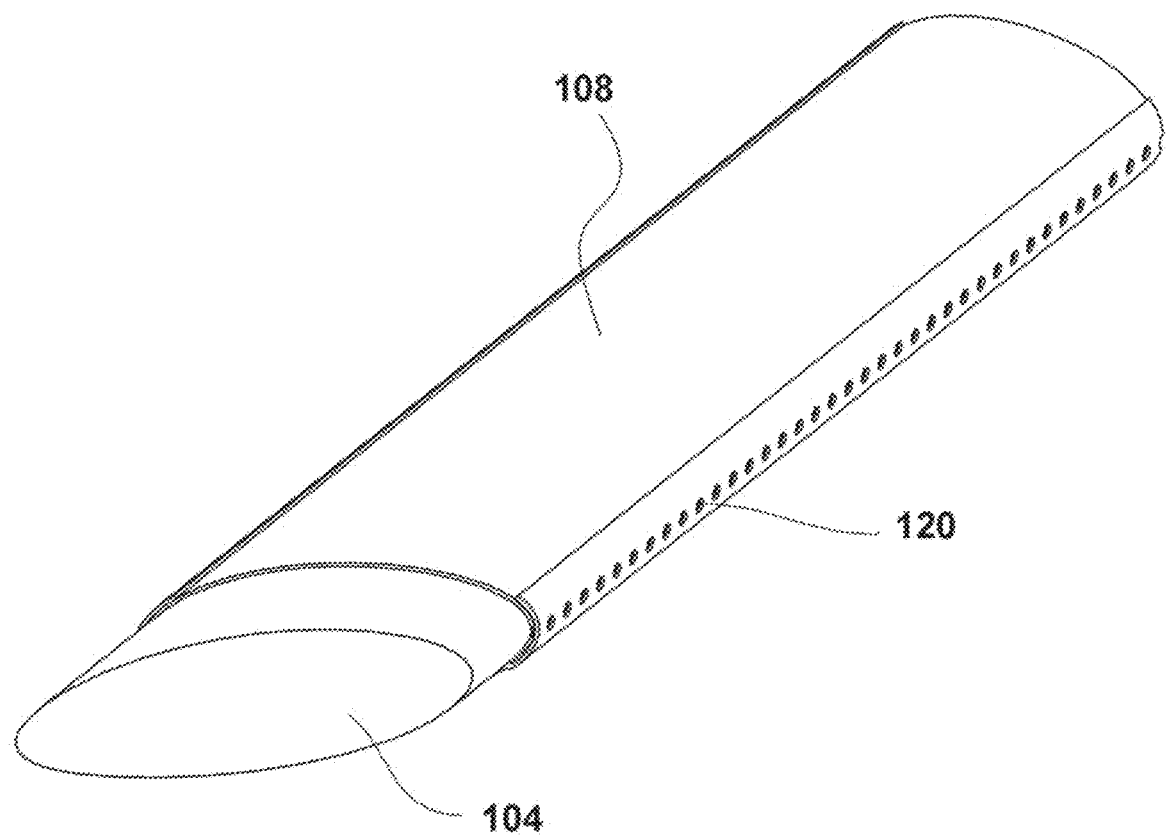
FIGS. 7A and 7B shown perspective views of other embodiments of the present invention.
Figure 7B:
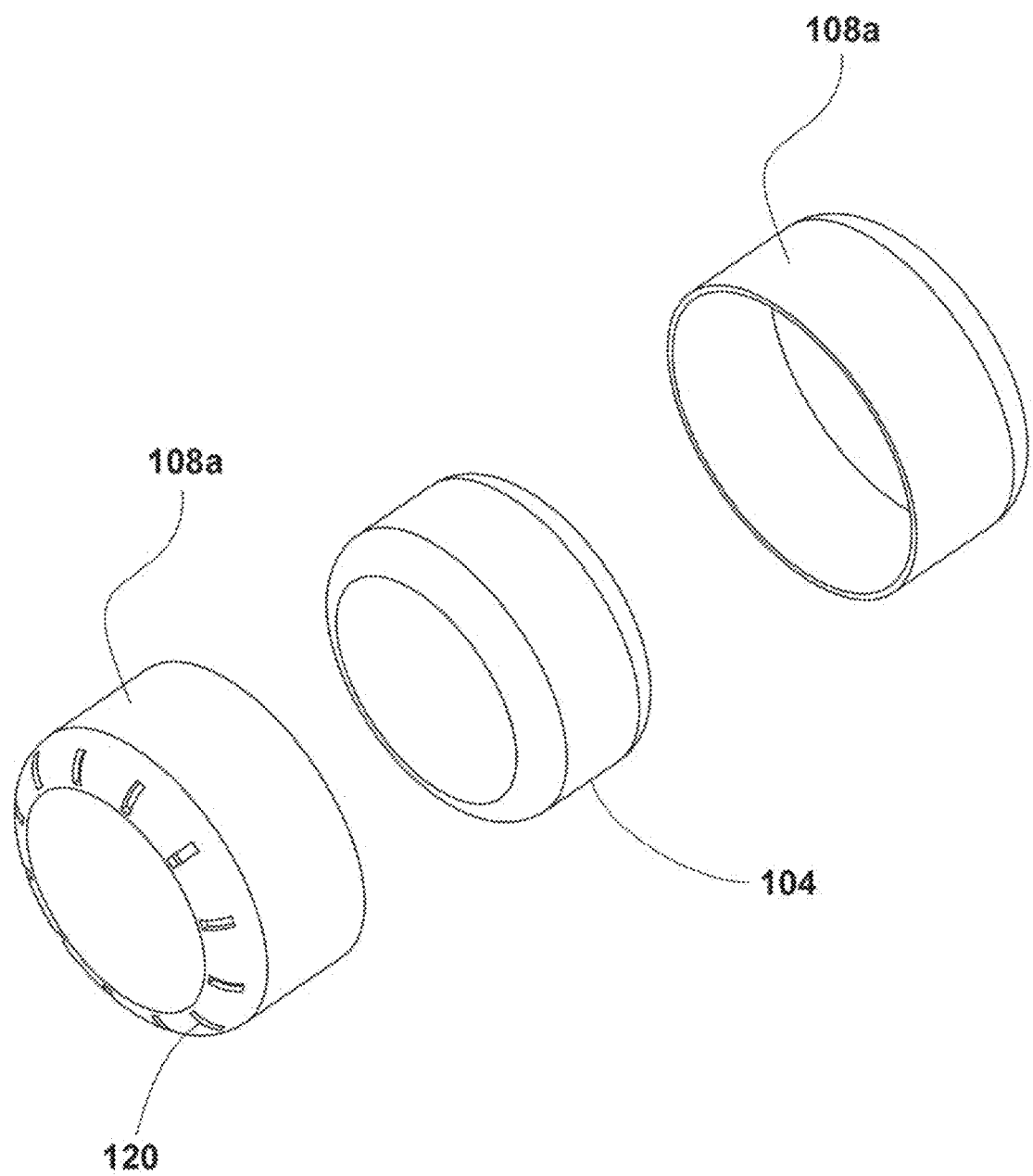

In some embodiments, as shown in FIGS. 7A-7D, the encasement 108 may be made out of material that allows the encasement 108 to serve as the susceptor. For example, the encasement 108 can be made of steel, or otherwise comprise ferrous metal, or any other metal that can be heated using induction heating. In such an embodiment, an interior susceptor 106 would not be required to be embedded into the consumable-containing unit 104. The encasement 108 can still comprise a plurality of holes 120, and be covered with an additive and/or sealant such as PGA. Such an embodiment can be made into an elongated tube as shown in FIG. 7A or into tablets or disks as shown in FIG. 7B. The encasement 108 can be a two piece encasement having a first encasement section 108*a* and a second encasement section 108*b* as discussed previously.

Figure 7C:
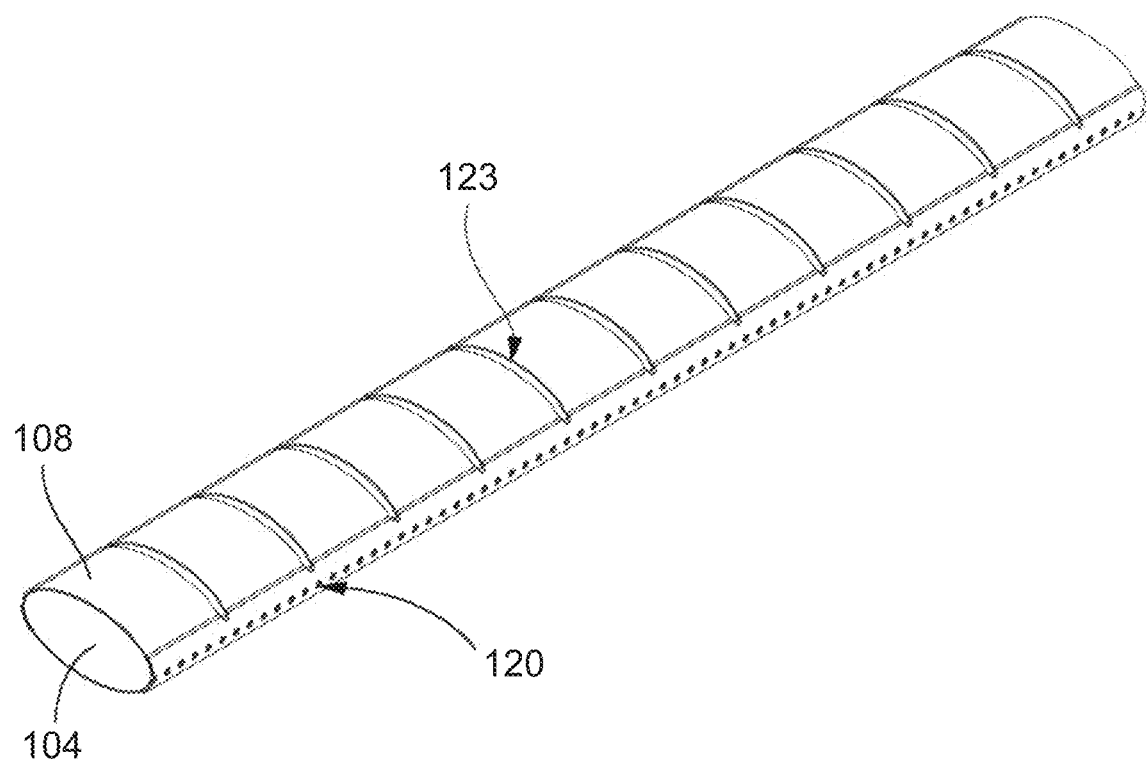
FIG. 7C shows another embodiment of the present invention.
Figure 7D:
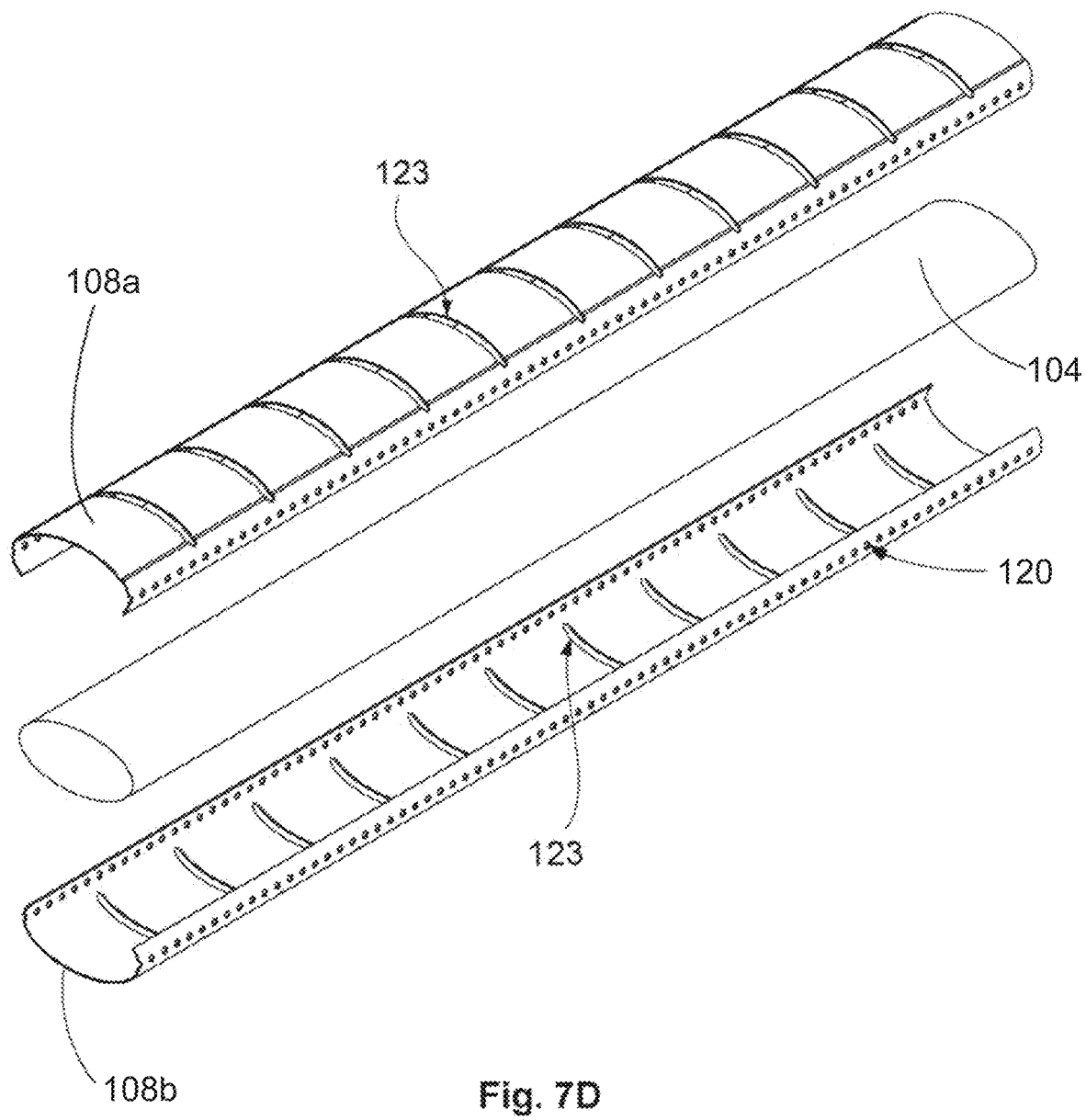
FIG. 7D shows an exploded view of the embodiment in FIG. 7C.

In some embodiments, the encasement 108 may have transverse slits 123 transversely across the encasement 108, generally perpendicular to the longitudinal axis L as shown in FIGS. 7C and 7D. The slits 123 create segmentation in the encasement 108 so that only a small segment of the consumable-containing unit 104 is heated per actuation. The transverse slits 123 may be through holes, which expose the consumable-containing unit 104 underneath. In such embodiments, the segments may be filled with a coating or some other plug to seal the hole, either permanently or with a substance that will melt upon heating and allow the aerosol to escape through the slit 123. In some embodiments, the plug may be made from material that can function as a heat sink and/or a substance that is not easily heated via induction to reduce the heating effect at the transverse slits 123. In some embodiments, the transverse slit 123 may be a recessed portion of or an indentation in the encasement 108. In other words, the transverse slit 123 may be a thinned portion of the encasement 108. As such, the transverse slit 123 may define a well. The well can be filled with a plug that can function as a heat sink and/or a substance that is not easily heated via induction to reduce the heat transfer along the transverse slit 123.

Induction Heating

Figure 8A:
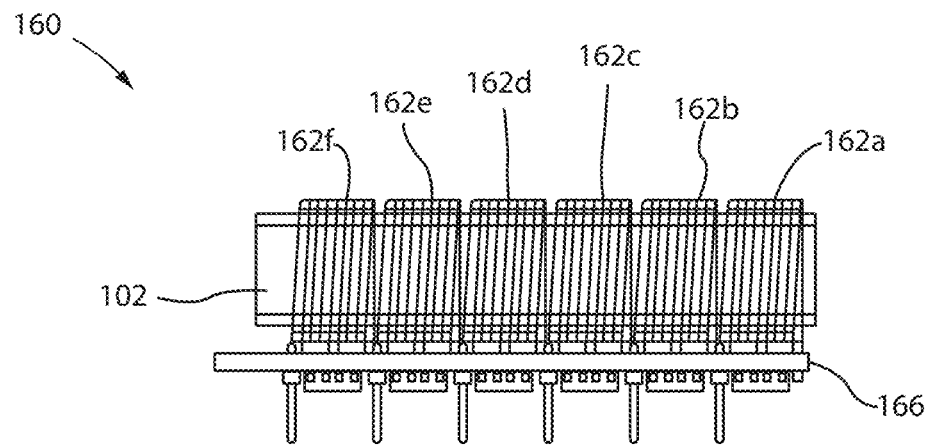
FIG. 8A shows a side view of an embodiment of the heating element.
Figure 8B:
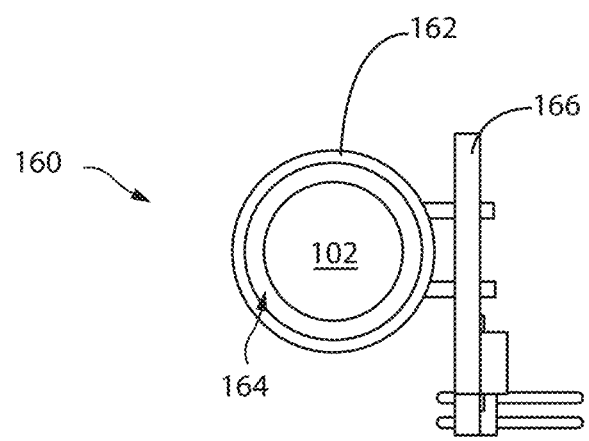
FIG. 8B shows a front view of the heating element shown in FIG. 7A.

Heating the consumable-containing unit 104 is achieved by an induction heating process that provides non-contact heating of a metal, preferably ferrous metal, by placing the metal in the presence of a varying magnetic field generated by an inductive heating element 160, as shown in FIGS. 8A-8B. In the preferred embodiment, inductive heating element 160 is a conductor 162 wrapped around into a coil that generates the magnetic field when current is passed through the coil. The metal susceptor 106 is placed close enough to the conductor 162 so as to be within the magnetic field. In the preferred embodiment, the coil is wrapped in a manner that defines a central cavity 164. This allows the consumable-containing package 102 to be inserted into the cavity 164 to have the coil surround the susceptor 106 without touching the susceptor 106. The current passed through the coil is alternating current creating a rapidly alternating magnetic field. The alternating magnetic field may create eddy currents in the susceptor 106, which may generate heat within the susceptor 106. Thus the consumable-containing package 102 is generally heated from the inside out. In embodiments in which the encasement 108 also serves as the susceptor, the consumable-containing package 102 is heated from the outside in.

In the preferred embodiment, segments of the consumable-containing package 102 are to be heated individually. As such, the conductor 162 may also be provided as individual sets of coiled conductors 162*a-f*, as shown in FIG. 8A. Each conductor coil 162*a-f* may be attached to a controller 166 that can be controlled to activate one conductor coil 162*a-f* at a time. Although there are six (6) conductor coils 162*a-f* shown in FIG. 8A, greater or fewer coils could be used. In an alternative embodiment, a single conductor coil 162 may be used, with a mechanical mechanism that translates the coil along the consumable-containing package 102 to individually heat each segment of the consumable-containing package 102.

The individual conductor coils 162*a-f* may match up with discrete segments of the consumable-containing package 102, as described above, and shown in FIGS. 3A-6B. Alternatively, the conductor coils 162*a-f* could each correspond to a certain length of a continuous consumable-containing package 102 such as shown in FIGS. 2A-2D, 7A, and 7D, to heat only that certain length. In preliminary testing of such embodiments, heating along discrete lengths of the consumable-containing package 102 does not appreciably heat adjacent portions of the consumable-containing package 102, as the adjacent non-heated consumable appears to act as an insulator. Thus, structures to limit heat transfer may not be necessary, although such structures have been discussed herein and may be useful.

The efficiency of conversion of electric power into thermal heat in the susceptor 106 is referred to herein as the "conversion efficiency," and is based on a variety of factors, such as bulk resistivity of the metal, dielectric of the metal, metal geometry and heat loss, power supply consistency and efficiency, coil geometry, and losses and overall frequency of operation—to identify some of these factors. The device 100 is designed and configured to maximize the conversion efficiency.

Aerosol Producing Device

Figure 9A:
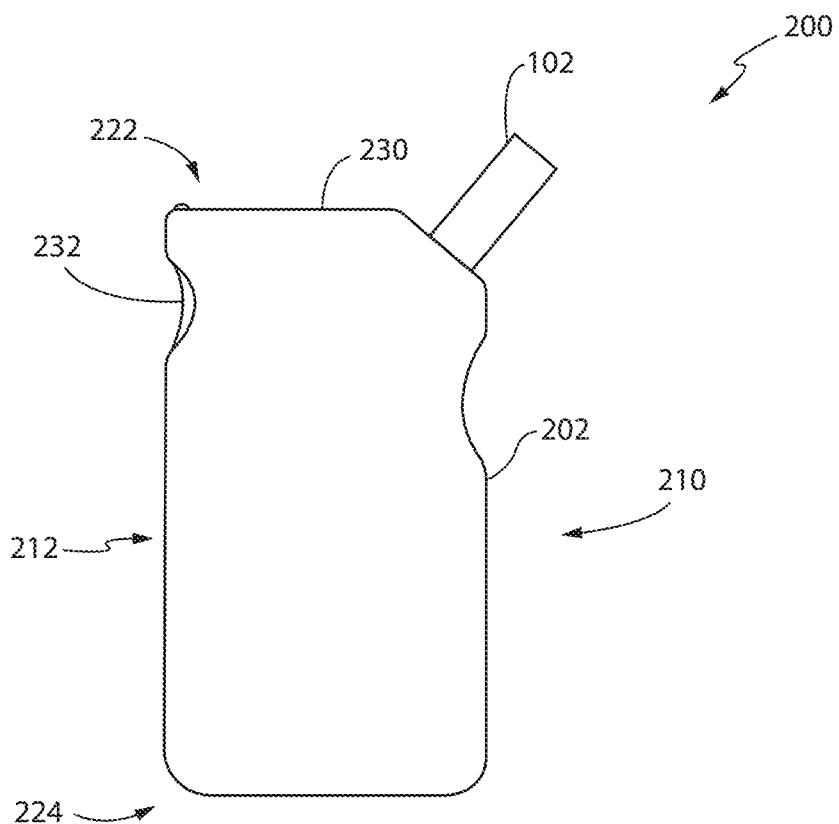
FIG. 9A shows a side view of an embodiment of the aerosol producing device.
Figure 9B:
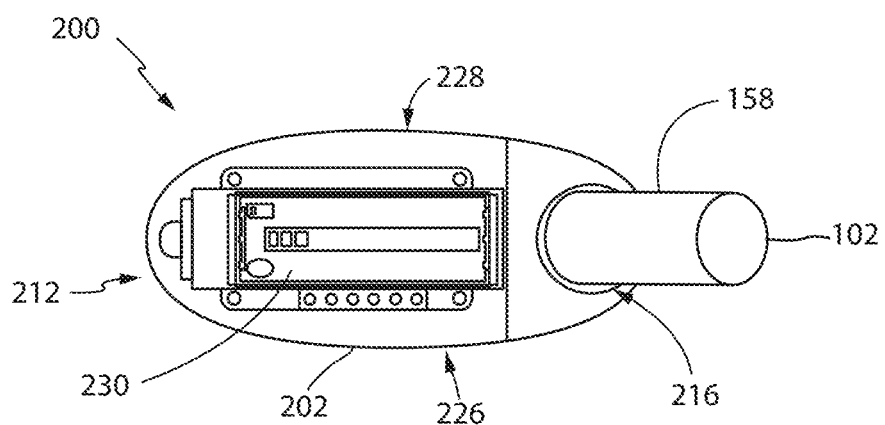
FIG. 9B shows a top view of the aerosol producing device shown in FIG. 8A.
Figure 9C:
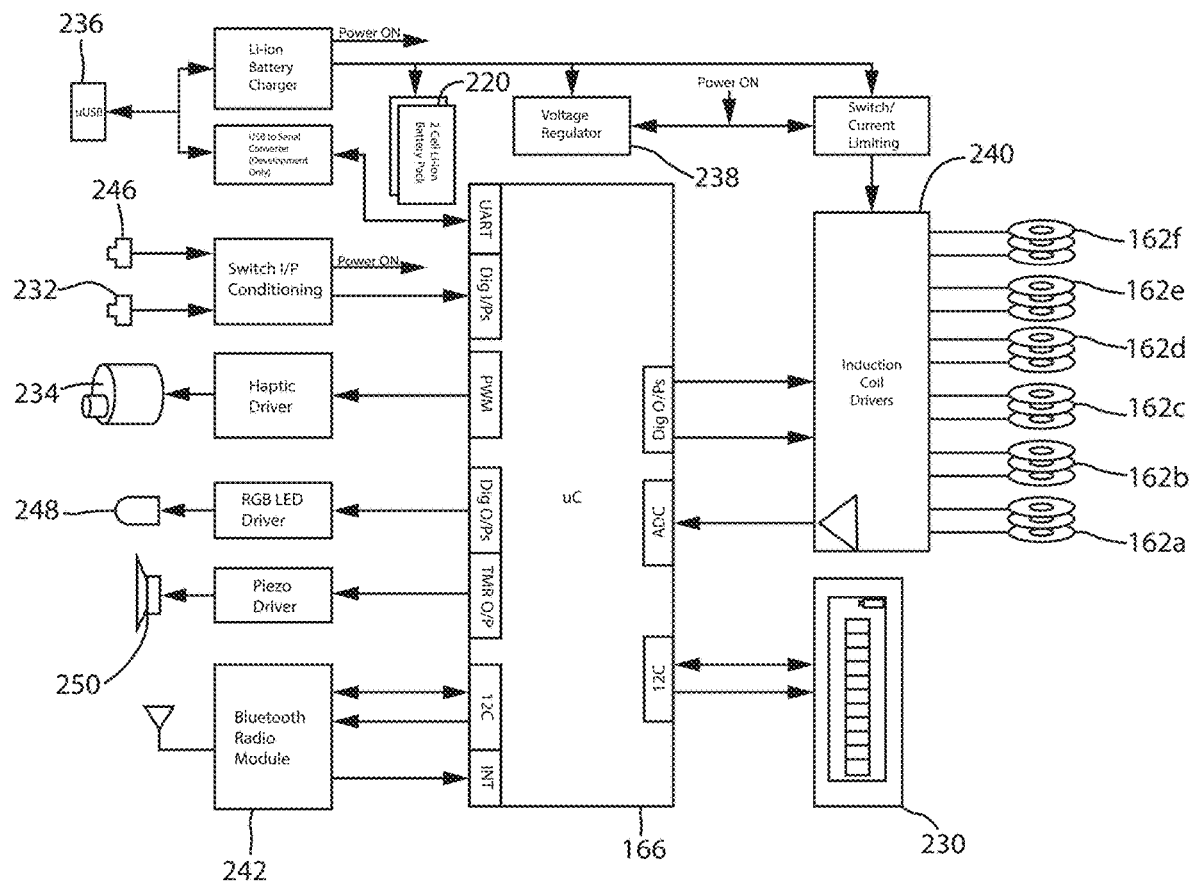
FIG. 9C shows a schematic diagram of an embodiment of the controller and its connection to other components of the present invention.

To effectuate the heating and conversion to an aerosol of the consumable, the housing 150 containing the filter tube 140 wrapped around the consumable-containing unit 104 is placed inside an aerosol producing device 200, as shown in FIGS. 9A-9C. The aerosol producing device 200 comprises a case 202 to contain the consumable-containing package 102, the induction heating element 160 to heat the susceptor 106, and a controller 166 to control the induction heating element 160.

The case 202 is designed for ergonomic use. For ease of nomenclature, the case 202 is described using terms such as front, back, sides, top and bottom. These terms are not meant to be limiting, but rather, used to describe the positions of various components relative to each other. For purposes of describing the present invention, the front 210 will be the portion of the case 202 that faces the user when used as intended as described herein. As intended, when the user grasps the case 202 for use, the fingers of the user will wrap around the back 212 of the device 100 with the thumb wrapping around the front 210.

The case 202 defines a cavity 214 (see FIG. 1) in which the components of the device 100 are contained. As such, the case 202 is designed to contain a substantial portion of the consumable-containing package 102, the controller 166, the inductive heating element 160, and the power source 220. In the preferred embodiment, the top-front portions of the case 202 defines an orifice 216. The mouthpiece portion 158 of the consumable-containing package 102 projects out from the orifice 216 so that the user has access to the consumable-containing package 102. The mouthpiece 158 projects sufficiently out of the case 202 to allow the user to place his or her lips around the mouthpiece 158 to inhale the consumable aerosol.

The case 202 is intended to be user-friendly and easily carried. In the preferred embodiment, the case 202 may have dimensions of approximately 85 mm tall (measured from top 222 to bottom 224) by 44 mm deep (measured from front 210 to back 212) by 22 mm wide (measured from side 226 to side 228). This may be manufactured by proto-molding for higher quality/sturdier plastic parts.

In some embodiments, the consumable-containing package 102 may be held in a retractor that allows the consumable-containing package 102 to be retracted inside the case 202 for storage and travel. Due to the configuration of the consumable-containing package 102, the case 202 does not need a clean-out through-hole like other devices in which some combustion is still prevalent creating byproduct residue from the combustion. In embodiments where the consumable-containing package 102 comprises a user mouthpiece 158 and filter tube 140, if there are any byproducts created during operation they will remain in the disposable consumable-containing package 102, which is changed out when the user inserts a new consumable-containing package 102, and filter tube 140 if necessary, into the case 202. Thus, the interior of case 202 stays clean during operation.

In the preferred embodiment, the top 222 of the case 202 comprises a user interface 230. Placing the user interface 230 at the top 222 of the case 202 allows the user to easily check the status of the device 100 prior to use. The user could potentially view the user interface 230 even while inhaling. The user interface 230 may be multi-color LED (RGB) display for device status indication during use. A light-pipe may be used to provide wide angle visibility of this display. By way of example only, user interface 230 has a 0.96 inch (diagonal) MED display with 128×32 format and I2C (or SPI) interface. The user interface 230 is capable of haptic feedback 234 (vibration) and audio feedback 250 (piezo-electric transducer). In some embodiments, a clear plastic (PC or ABS) cover may be placed over the OLED glass to protect it from damage/scratches.

The back 212 of the case comprises a trigger 232, which is a finger activated (squeeze) button to turn the device on/initiate "puff." Preferably, the trigger 232 is adjacent to the top 212. In this configuration, the user can hold the case 202 as intended with his or her index finger on or near the trigger 232 for convenient actuation. In some embodiments, a locking mechanism may be provided on the trigger 232—either mechanically or through electrical interlock that requires the case 202 to be opened before the trigger 232 is electrically enabled. In some embodiments, a haptic feedback motor 234 may be mechanically coupled to the trigger 232 to improve recognition of haptic feedback by the user during operation. Actuation of the trigger 232 powers the induction heating element 160 to heat the susceptor 106.

The device 100 is powered by a battery 220. Preferably, the battery 220 is a dual cell Li-ion battery pack (series connected) with 4A continuous draw capability, and 650-750 mAh rated. The dual cell pack may include protection circuit. The battery 220 can be charged with a USB Type "C" connector 236. The USB type "C" connector 236 can also be used for communications. The controller 166 may also provide for battery voltage monitoring 238 for battery state of charge/discharge display.

The trigger 232 is operatively connected to the induction coil driver 240 via the controller 166. The induction coil driver 240 activates the inductive heating element 160 to heat the susceptor 106. The present invention eliminates the motor driven coil design in the prior art. The induction coil driver 240 can provide drive/multiplexing for multiple coils. For example, the induction coil driver 240 may provide drive/multiplexing for 6 or more coils. Each coil is wrapped around one segment of the consumable-containing package 102 and can be actuated at least one or more times. Therefore, one segment of the consumable-containing package 102 can be heated twice, for example. In a device 100 having six coils, the user could extract 12 "puffs" from the device 100.

The induction coil drive circuit in the preferred embodiment may be directly controlled by a microprocessor controller 166. A special peripheral in this processor (Numerically Controlled Oscillator) allows it to generate the frequency drive waveforms with minimal CPU processing overhead. The induction coil circuit may have one or more parallel connected capacitors, making it a parallel resonant circuit.

The drive circuit may include current monitoring with a "peak detector" that feeds back to an analog input on the processor. The function of the peak detector is to capture the maximum current value for any voltage cycle of the drive circuit providing a stable output voltage for conversion by an analog-to-digital converter (part of the microprocessor chip) and then used in the induction coil drive algorithm.

The induction coil drive algorithm is implemented in firmware running on the microprocessor. The resonant frequency of the induction coil and capacitors will be known with reasonable accuracy by design as follows:

$$\text{Frequency of resonance (in Hertz)} = 1/(2*pi*\text{SQRT}\{L*C\})$$

where: $pi = 3.1415\ldots$,

SQRT indicates the square root of the contents in the brackets $\{\ldots\}$,

L = the measured inductance of the induction coil, and

C = the known capacitance of the parallel connected capacitors.

There will be manufacturing tolerances to the values of L and C (from above), which will produce some variation in the actual resonant frequency versus that which is calculated using the formula above. Additionally, there will be variation in the inductance of the induction coil based on what is located inside of this coil. In particular, the presence of a ferrous metal inside (or in the immediate vicinity) of this coil will result in some amount of inductance change resulting in a small change in the resonant frequency of the L-C circuit.

The firmware algorithm for driving the induction coil will sweep the frequency of operation over the maximum expected frequency range, while simultaneously monitoring the current, looking for the frequency where the current draw is at a minimum. This minimum value will occur at the frequency of resonance. Once this "center frequency" is found, the algorithm will continue to sweep the frequency by a small amount on either side of the center frequency and adjust the value of the center frequency as required to maintain the minimum current value.

The electronics are connected to the controller 166. The controller 166 allows for a processor based control of frequency to optimize heating of the susceptor 106. The relationship between frequency and temperature seldom correlates in a direct way, owing in large part to the fact that temperature is the result of frequency, duration and the manner in which the consumable-containing package 102 is configured. The controller 166 may also provide for current monitoring to determine power delivery, and peak voltage monitoring across the induction coil to establish resonance. By way of example only, the controller may provide a frequency of approximately 400 kHz to approximately 500 kHz, and preferably, 440 kHz with a three-second pre-heat cycle to bring the temperature of the susceptor 106 to 400 degrees Celsius or higher in one second. In some embodiments, the temperature of the susceptor 106 can be raised to 550 degrees Celsius or higher in one second. In some embodiments, the temperature can be raised as high as 800 degrees Celsius. Thus, the present invention has an effective range of 400-800 degrees Celsius. In prior art devices, such temperatures would combust the consumable, making the prior art devices ineffective at these temperatures. In the present invention, such high temperatures can still be used to improve the efficiency of aerosol production and allow for quicker heat times.

The device 100 may also comprise a communications system 242. In the preferred embodiment, Bluetooth low energy radio may be used to communicate with a peripheral device. The communications system 242 may serial interface to the main processor for communicating information with a phone, for example. Off-the-shelf RF module (pre-certified: FCC, IC, CE, MIC) can also be used. One example utilizes Laird BL652 module because SmartBasic support allows for rapid application development. The communication system 242 allows the user to program the device 100 to suit personal preferences related to the aerosol density, the amount of flavor released, and the like by controlling the frequency and the 3-stage duty cycle, specifically, the pre-heat stage, heating stage, and wind-down stage of the inductive heating elements 160. The communication system 242 may have one or more USB ports 236.

In some embodiments, an RTC (Real-time Clock/Calender) with battery back-up may be used to monitor usage information. The RTC can measure and store relevant user data to be used in conjunction with an external app downloaded on to a peripheral device, such as a smartphone.

In some embodiments, a micro-USB connector (or USB type C connector or other suitable connector) may be located on the bottom of the case 202. Support connector with plastics may be provided on all sides to reduce stress on connector due to cable forces.

By way of example only, the device 100 may be used as follows. Power for the device may be turned on from momentary actuation of the trigger 232. For example, a short press of the trigger (<1.5 sec) may turn the device 100 on but does not initiate the heating cycle. A second short press of the trigger 232 (<1 sec) during this time will keep the device 100 on for a longer period of time and initiate Bluetooth advertising if no active (bonded) Bluetooth connection with phone currently exists. A longer press of the trigger 232 (>1.5 sec) initiates the heating cycle. The power for the device 100 may remain on for a short period of tune after each heating cycle (e.g., 5 sec) to display updated unit status on the OLED user interface 230 before powering off. In some embodiments, the device 100 may power on when the consumable-containing package 102 is deployed from the case 202. In some embodiments, a separate power switch 246 may be used to turn the device on and off.

When an active connection is found with a smartphone and the custom application is running on the smartphone, then the device 100 will remain powered on for up to 2 minutes before powering off. When the battery level too low to operate, the user interface display 230 flashes several times (showing battery icon at "0%" level) before turning unit off.

In some embodiments, the user interface 230 may display a segmented cigarette showing which segments remain (solid fill) versus which segments have been used (dotted outline) as an indicator of how much of the consumable-containing package 102 still contains consumable products to be released. The user interface 230 can also display a battery icon updated with current battery status, charging icon (lightning bolt) when the device is plugged in, and a Bluetooth icon when active connection exists with a smartphone. The user interface 230 may show the Bluetooth icon flashing slowly when no connection exists hut the device 100 is advertising.

The device may also have an indicator 248 to inform the user of the power status. The indicator 248 may be an RGB LED. By way of example only, the RGB LED can show a green LED on when the device is first powered on, a red LED flashing during the preheat time, a red LED on (solid) during the "inhale" time, and a blue LED flashing during charging. Duty cycle of flashing indicates the battery's relative state of charge (20-100%) in 20% increments (solid blue means fully charged). A fast flashing of blue LED may be presented when an active Bluetooth connection is detected (phone linked to device and custom app on phone is running).

Haptic feedback can provide additional information to the user during use. For example, 2 short pulses can be signaled immediately when power is turned on (from finger trigger button). An extended pulse at the end of preheat cycle can be signaled to indicate the devices refer inhalation (start of HNB "inhale" cycle). A short pulse can be signaled when USB power is first connected or removed. A short pulse can be signaled when an active Bluetooth connection is established with an active phone app running on the smartphone.

A Bluetooth connection can be initiated after power is turned on from a short (<1.5 sec) press of the finger grip button. If no "bonded" BLE (Bluetooth Low Energy) connection exists, that the devices may begin slow advertising ("pairing" mode) once a second short press is detected after initial short press is detected that powers the device on. Once a connection is established with the smartphone application, the Bluetooth icon on the user interface display 230 may stop flashing and the blue LED will turn on (solid). If the device 100 is powered on and it has a "bonded" connection with a smartphone, then it may begin advertising to attempt to re-establish this connection with the phone up until it powers off. If the connection with this smartphone is able to be re-established, then the unit may remain powered on for up to 2 minutes before powering itself off. To delete a bonded connection, the user can power the device on with a short press followed by another short press. While BLE icon is flashing, the user can press and hold the trigger 232 until the device 100 vibrates and the Bluetooth icon disappears.

So, by tight control of the afore-mentioned conversion efficiency factors and the product consistency factors, it is possible to provide controlled delivery of heat to the consumable-containing unit 104. This controlled delivery of heat involves a microprocessor controller 166 for the monitoring of the induction heating system 160 to maintain various levels of electrical power delivery to the susceptor 106 over controlled intervals of time. These properties enable a user-control feature that would allow the selection of certain consumable flavors as determined by the temperature at which the consumable aerosol is produced.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A device, comprising:
   a) a compressed consumable-containing unit;
   b) a susceptor embedded within the compressed consumable-containing unit;
   c) an encasement encasing the compressed consumable-containing unit and the susceptor, wherein the encasement comprises an opening; and
   d) a filter configured to surround the encasement in a manner that eliminates a gap between the filter and the encasement.

2. The device of claim 1, further comprising a housing to contain the encasement.

3. The device of claim 2, further comprising an inductive heating element configured and programmed to selectively heat the susceptor to a predetermined temperature, the predetermined temperature being sufficient to release aerosol from the compressed consumable-containing unit.

4. The device of claim 3, further comprising an aerosol producing device configured to hold the housing and the inductive heating element, the housing comprising a mouthpiece projecting out from the aerosol producing device, the aerosol producing device comprising:
   a) a case to contain the inductive heating element;
   b) a switch mounted on the case, the switch operatively connected to the inductive heating element to activate the inductive heating element,
   c) a user interface operatively coupled with the switch and the inductive heating element to provide status information; and
   d) a controller, comprising a processor based control of frequency delivered to the inductive heating element.

5. The device of claim 4, wherein the housing is configured to isolate from the case an aerosol released from the encasement.

6. A device, comprising:
   a) a compressed consumable-containing unit;
   b) a susceptor embedded within the compressed consumable-containing unit;
   c) an encasement encasing the compressed consumable-containing unit and the susceptor, wherein the encasement comprises an opening, wherein the encasement comprises a first end and a second end, and wherein one of the first or second ends of the encasement comprises a fold to space apart adjacent encasements.

7. A device, comprising:
   a) a compressed consumable-containing unit;
   b) a susceptor embedded within the compressed consumable-containing unit;
   c) an encasement encasing the compressed consumable-containing unit and the susceptor;
   d) a plurality of openings on the encasement; and
   e) a coating to cover the plurality of openings.

8. The device of claim 7, wherein the coating comprises propylene glycol alginate.

9. The device of claim 7, wherein the coating comprises a flavoring.

10. The device of claim 1, wherein the susceptor is sandwiched in between two pellets of compressed consumable-containing units.

11. The device of claim 1, wherein the susceptor is a metal plate.

12. The device of claim 11, wherein the metal plate comprises a plurality of openings.

13. The device of claim 11, wherein the susceptor is an elongated metal plate having a longitudinal direction, the elongated metal plate comprising sets of openings, and sets of gaps, wherein the sets of openings alternate in series with the sets of gaps along the longitudinal direction of the elongated metal plate such that each set of openings is adjacent to one of the gaps.

14. The device of claim 1, wherein the susceptor comprises steel wool.

15. The device of claim 14, wherein the susceptor comprises an additive.

16. The device of claim 14, wherein the susceptor is an elongated pad having a longitudinal direction, the elongated pad comprising sets of openings, and sets of gaps, wherein the sets of openings alternate in series with the sets of gaps along the longitudinal direction of the elongated pad such that each set of openings is adjacent to one of the gaps.

17. A method of using a device comprising a compressed consumable-containing unit, a susceptor embedded within the compressed consumable-containing unit, and an encasement encasing the compressed consumable-containing unit and the susceptor, wherein the encasement comprises an opening, the method comprising:
   a) releasing an aerosol form of a consumable from the compressed consumable-containing unit without producing toxic byproducts associated with combustion;
   b) applying heat to the compressed consumable-containing unit by heating the susceptor with an induction heating element to release the aerosol form of the consumable from the compressed consumable-containing unit without combusting the compressed consumable-containing unit; and
   c) melting a coating on the encasement to release the consumable in aerosol form from the encasement through openings in the encasement.

18. A method of manufacturing a device for generating an inhalable aerosol, the method comprising:
   a) compressing a consumable-containing unit around a susceptor;
   b) placing the consumable-containing unit and the susceptor into an encasement;
   c) placing the encasement containing the consumable-containing unit into a housing; and
   d) applying a coating onto openings in the encasement, whereby the device for generating an inhalable aerosol is manufactured.

19. A method of manufacturing a device for generating an inhalable aerosol, the method comprising:
   a) compressing a consumable-containing unit around a susceptor;
   b) placing the consumable-containing unit and the susceptor into an encasement;
   c) placing the encasement containing the consumable-containing unit into a housing; and
   d) placing the encasement into a filter tube, whereby the device for generating an inhalable aerosol is manufactured.

20. The method of claim 19, further comprising providing an aerosol producing device having an inductive heating element for receiving the housing.

21. The method of claim 19, further comprising surrounding the filter tube, the encasement, the consumable-containing unit, and the susceptor, with an inductive heating element.

22. The method of claim 19, further comprising stacking a plurality of encasements inside the filter tube, wherein each encasement comprises a respective consumable-containing unit.

23. The method of claim 19, further comprising mixing the consumable-containing unit with an additive prior to compressing the consumable-containing unit onto the susceptor to minimize oxygen within the consumable-containing unit.

\* \* \* \* \*